United States Patent
Yamamoto et al.

(10) Patent No.: US 10,534,236 B2
(45) Date of Patent: Jan. 14, 2020

(54) ELECTROCHROMIC COMPOUND, ELECTROCHROMIC COMPOSITION, AND ELECTROCHROMIC DISPLAY ELEMENT

(71) Applicants: Satoshi Yamamoto, Kanagawa (JP); Daisuke Goto, Kanagawa (JP); Toshiya Sagisaka, Kanagawa (JP); Masato Shinoda, Kanagawa (JP); Mamiko Inoue, Kanagawa (JP); Fuminari Kaneko, Kanagawa (JP); Tohru Yashiro, Kanagawa (JP)

(72) Inventors: Satoshi Yamamoto, Kanagawa (JP); Daisuke Goto, Kanagawa (JP); Toshiya Sagisaka, Kanagawa (JP); Masato Shinoda, Kanagawa (JP); Mamiko Inoue, Kanagawa (JP); Fuminari Kaneko, Kanagawa (JP); Tohru Yashiro, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 79 days.

(21) Appl. No.: 15/737,115

(22) PCT Filed: Jun. 17, 2016

(86) PCT No.: PCT/JP2016/002923
§ 371 (c)(1),
(2) Date: Dec. 15, 2017

(87) PCT Pub. No.: WO2016/203773
PCT Pub. Date: Dec. 22, 2016

(65) Prior Publication Data
US 2018/0173070 A1    Jun. 21, 2018

(30) Foreign Application Priority Data

Jun. 19, 2015 (JP) .................................. 2015-123939
Apr. 19, 2016 (JP) .................................. 2016-083873

(51) Int. Cl.
*G02F 1/15* (2019.01)
*C07D 265/28* (2006.01)
(Continued)

(52) U.S. Cl.
CPC .............. *G02F 1/15* (2013.01); *C07D 265/28* (2013.01); *C07D 265/38* (2013.01); *C08F 20/36* (2013.01);
(Continued)

(58) Field of Classification Search
CPC ............................ C07D 265/28; C07D 265/38
See application file for complete search history.

(56) References Cited

U.S. PATENT DOCUMENTS

| | | | | |
|---|---|---|---|---|
| 4,505,844 A | * | 3/1985 | Denisevich, Jr. ..... | C08G 61/122 252/500 |
| 5,942,615 A | * | 8/1999 | Kobayashi ........... | C07D 265/38 430/58.5 |

(Continued)

FOREIGN PATENT DOCUMENTS

| JP | 2003007466 A | * | 1/2003 |
|---|---|---|---|
| JP | 2003165829 A | * | 6/2003 |

(Continued)

OTHER PUBLICATIONS

Machine translation of JP2003165829A, retrieved May 2019 (Year: 2019).*

(Continued)

*Primary Examiner* — Nicole M. Buie-Hatcher
(74) *Attorney, Agent, or Firm* — Oblon, McClelland, Maier & Neustadt, L.L.P.

(57) ABSTRACT

Provided is an electrochromic compound represented by the following general formula (I) or (II) where $R_1$ to $R_{13}$ are each independently a hydrogen atom, a halogen atom, a monovalent organic group, or a polymerizable functional
(Continued)

group, and at least one of the $R_1$ to the $R_{13}$ is a polymerizable functional group.

12 Claims, 3 Drawing Sheets

(51) Int. Cl.
| | | |
|---|---|---|
| *G09F 9/30* | (2006.01) | |
| *C09K 9/02* | (2006.01) | |
| *C08F 20/36* | (2006.01) | |
| *C07D 265/38* | (2006.01) | |
| *G02F 1/1516* | (2019.01) | |

(52) U.S. Cl.
CPC .............. *C09K 9/02* (2013.01); *G02F 1/1516* (2019.01); *G09F 9/30* (2013.01); *C09K 2211/1003* (2013.01); *C09K 2211/1007* (2013.01); *C09K 2211/1011* (2013.01); *C09K 2211/1033* (2013.01)

(56) References Cited

U.S. PATENT DOCUMENTS

| | | | | |
|---|---|---|---|---|
| 6,249,349 | B1* | 6/2001 | Lauer | G02B 21/00 |
| | | | | 356/450 |
| 6,870,657 | B1 | 3/2005 | Fitzmaurice et al. | |
| 2001/0026879 | A1* | 10/2001 | Chen | C08F 246/00 |
| | | | | 428/690 |
| 2005/0128561 | A1 | 6/2005 | Fitzmaurice et al. | |
| 2005/0128562 | A1 | 6/2005 | Fitzmaurice et al. | |
| 2006/0050357 | A1 | 3/2006 | Gavrilov et al. | |
| 2007/0259782 | A1 | 11/2007 | Yamamoto et al. | |
| 2008/0167465 | A1 | 7/2008 | Fitzmaurice et al. | |
| 2009/0230386 | A1 | 9/2009 | Yamamoto et al. | |
| 2010/0286360 | A1 | 11/2010 | Kobayashi et al. | |
| 2011/0045412 | A1* | 2/2011 | Kaneko | C08F 290/00 |
| | | | | 430/321 |
| 2013/0253131 | A1 | 9/2013 | Yamamoto et al. | |
| 2015/0331295 | A1 | 11/2015 | Takahashi et al. | |
| 2017/0342031 | A1* | 11/2017 | Suzuki | C09B 11/24 |
| 2018/0113366 | A1* | 4/2018 | Kaneko | G02F 1/13439 |

FOREIGN PATENT DOCUMENTS

| | | |
|---|---|---|
| JP | 2006-500635 A | 1/2006 |
| JP | 2008-001827 A | 1/2008 |
| JP | 2015-215552 A | 12/2015 |
| WO | WO 01/27690 A2 | 4/2001 |
| WO | WO2007/020954 A1 | 2/2007 |
| WO | WO2011/149056 A1 | 12/2011 |
| WO | WO-2016046077 A1 * | 3/2016 ............ C07F 9/5728 |

OTHER PUBLICATIONS

Machine translation of JP2008001827A, retrieved May 2019 (Year: 2019).*
International Search Report dated Aug. 9, 2016 for counterpart International Patent Application No. PCT/JP2016/002923 filed Jun. 17, 2016.
Written Opinion of the International Searching Authority dated Aug. 9, 2016 for counterpart International Patent Application No. PCT/JP2016/002923 filed Jun. 17, 2016.
Li, Mei, et al., "*Highly contrasted and stable electrochromic device based on well-matched viologen and triphenylamine*", Organic Electronics, 2014, 15, pp. 428-434.
Extended European Search Report dated Feb. 27, 2018 in Patent Application No. 16811248.0, 7 pages.
Japanese Office Action (Notice of Reasons for Refusal) dated Nov. 5, 2019, in Japanese Patent Application No. 2016-083873 (with English Translation).

* cited by examiner

[Fig. 1]
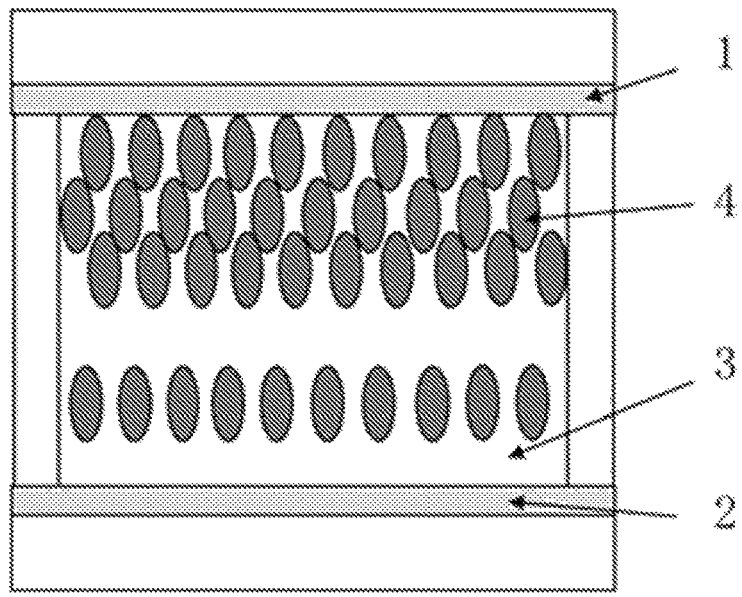
[Fig. 2]
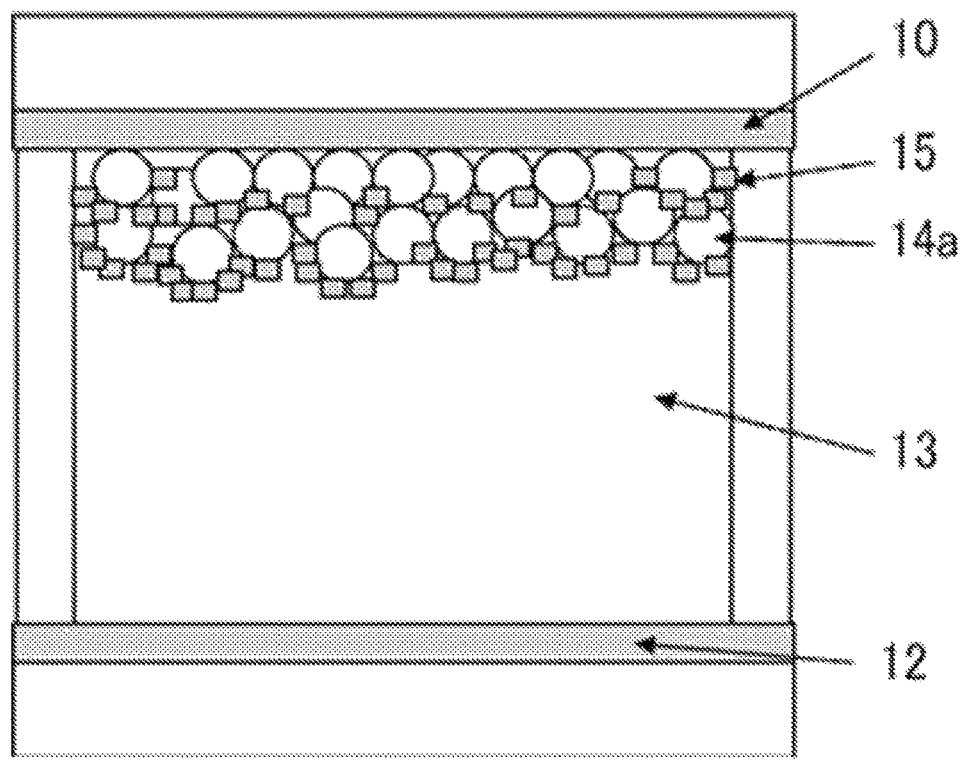

[Fig. 3]
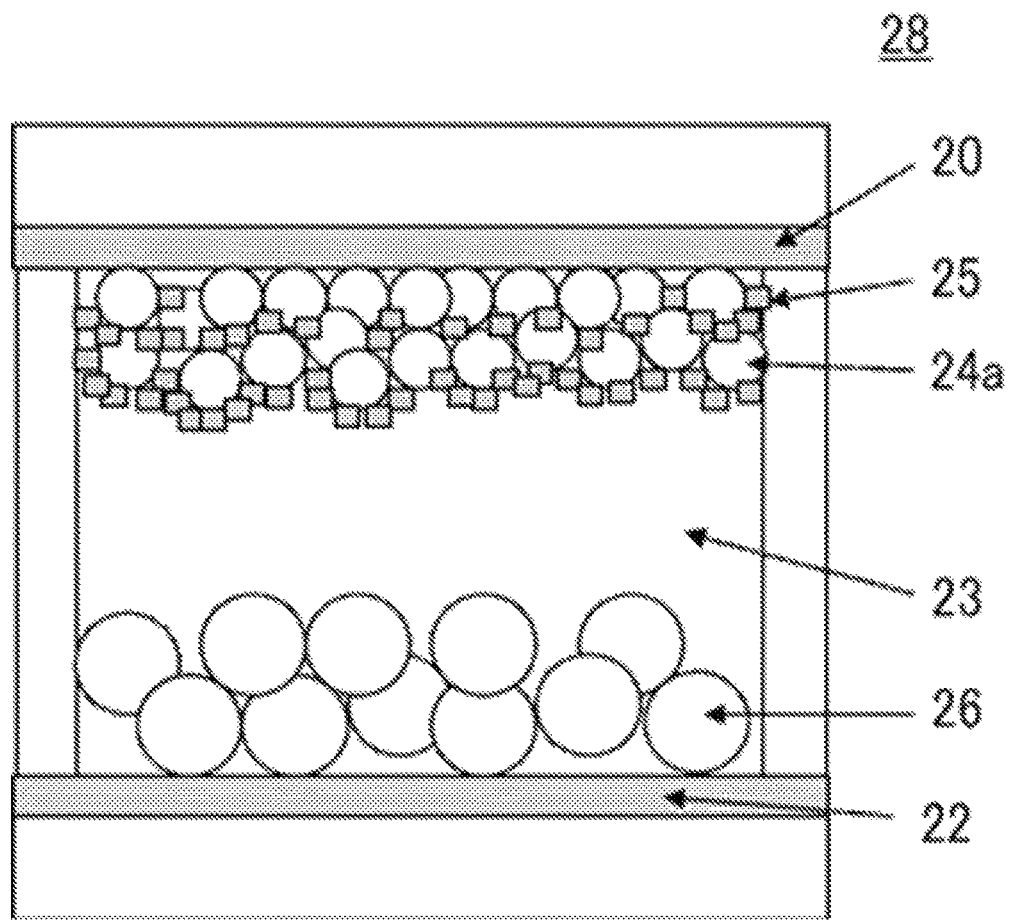
[Fig. 4]
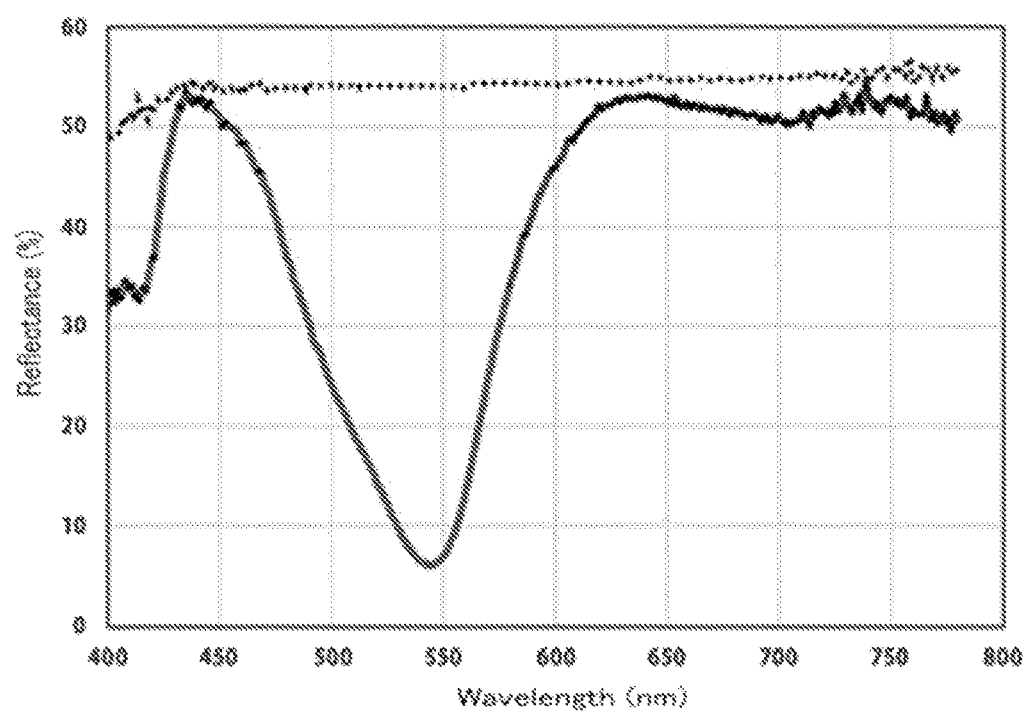

[Fig. 5]
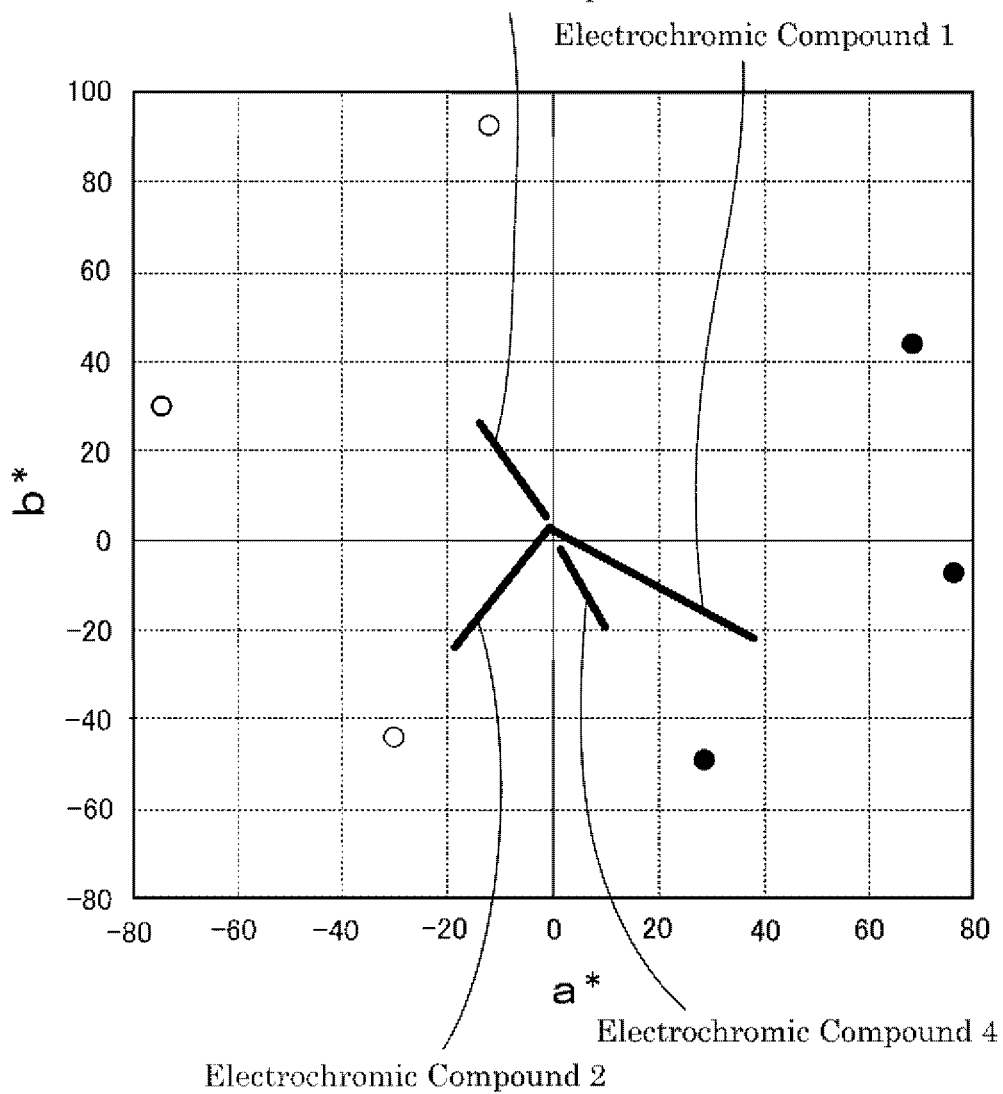

ELECTROCHROMIC COMPOUND, ELECTROCHROMIC COMPOSITION, AND ELECTROCHROMIC DISPLAY ELEMENT

TECHNICAL FIELD

The present disclosure relates to electrochromic compounds, electrochromic compositions, and electrochromic display elements.

BACKGROUND ART

Electrochromism is a phenomenon where an oxidation-reduction reaction is reversibly caused to reversibly change a color by applying voltage. An electrochromic material exhibiting the electrochromism is typically formed between two facing electrodes, and an oxidation-reduction reaction of the electrochromic material is caused in a structure where a space between the electrodes is filled with an electrolyte layer capable of conducting ions. When a reduction reaction occurs adjacent to one of the two facing electrodes, an oxidation reaction, which is a reverse reaction of the reduction reaction, occurs adjacent to the other electrode.

When voltage is applied, coloring occurs at both the electrodes in a device using the electrochromic material, to thereby change a color or optical density.

In a case where a transparent display device is produced with an electrochromic display element using the electrochromic material, or a case where a device having a structure, in which three coloring layers of cyan (C), magenta (M), and yellow (Y) are laminated, is produced with the electrochromic display element, it is important that the electrochromic display element is composed of a material that can be in a state of colorless transparent. As the electrochromic material that can exhibit such a state, reported are viologen compounds and triaryl amine compounds exhibiting an electrochromic phenomenon where a neutral state is a transparent state and coloring occurs in a reduced state (see, for example, NPL 1).

However, coloring of the triaryl amine compounds disclosed in NPL 1 is from blue to cyan or green, and it is difficult to obtain stable coloring of yellow (Y) or magenta (M).

CITATION LIST

Non Patent Literature

NPL 1: Org. Electron. 2014, 15, 428-434.

SUMMARY OF INVENTION

Technical Problem

The present invention has an object to provide an electrochromic compound that exhibits excellent color and has excellent durability to repetitive use.

Solution to Problem

As means for solving the aforementioned problems, the electrochromic compound of the present invention is a compound represented by the following general formula (I) or (II).

[Chem. 1]

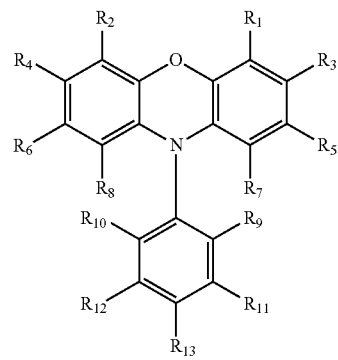

General formula (I)

[Chem. 2]

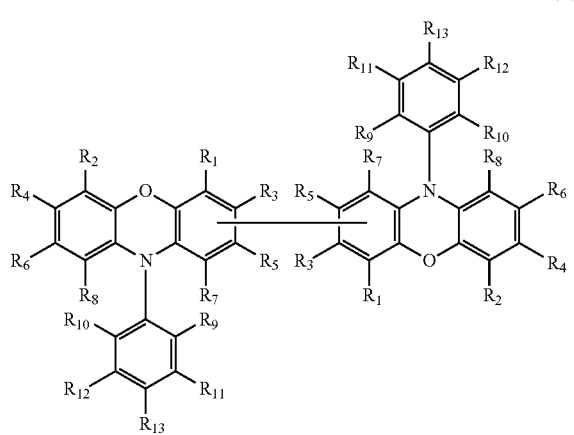

General formula (II)

In the general formulae (I) and (II), $R_1$ to $R_{13}$ are each independently a hydrogen atom, a halogen atom, a monovalent organic group, or a polymerizable functional group, and at least one of the $R_1$ to the $R_{13}$ is a polymerizable functional group.

Advantageous Effects of Invention

The present invention can provide an electrochromic compound that exhibits excellent color and has excellent durability to repetitive use.

BRIEF DESCRIPTION OF DRAWINGS

FIG. 1 is a schematic view illustrating an example of an electrochromic display element of the present invention.

FIG. 2 is a schematic view illustrating another example of an electrochromic display element of the present invention.

FIG. 3 is a schematic view illustrating another example of an electrochromic display element of the present invention.

FIG. 4 depicts transmission spectrums of the electrochromic display element of Example 8 at the time of decoloring and coloring.

FIG. 5 is a diagram depicting chromaticity coordinates of Electrochromic Compounds 1 to 4.

DESCRIPTION OF EMBODIMENTS (Electrochromic Compound)

An electrochromic compound of the present invention is represented by the following general formula (I) or (II).

[Chem.3]

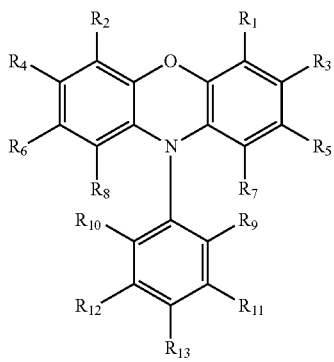

General formula (I)

[Chem.4]

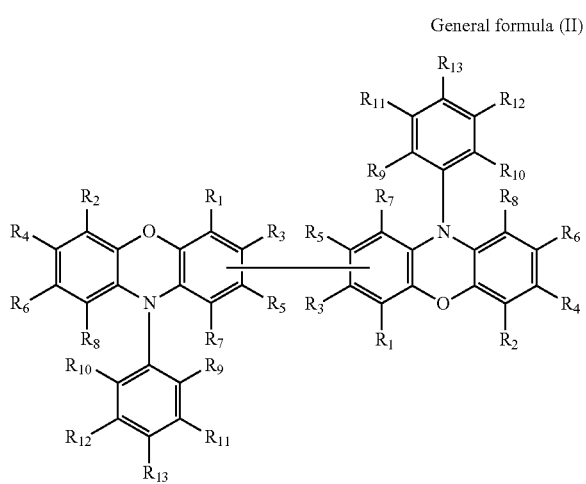

General formula (II)

In the general formula (I) and the general formula (II), $R_1$ to $R_{13}$ are each independently a hydrogen atom, a halogen atom, a monovalent organic group, or a polymerizable functional group, and at least one of the $R_1$ to the $R_{13}$ is a polymerizable functional group.

The present inventors have diligently studied the fact that coloring of a compound having triphenyl amine skeleton is from blue to cyan or green, and it is difficult to stably attain coloring of yellow (Y) or magenta (M). As a result, it has been found that (1) the triphenyl amine skeleton has phenyls bonded via a nitrogen atom (N) together through a nonconjugated bond, and thus even when the triphenyl amine skeleton is modified with substituents, a contribution of electron donating-withdrawing to pi conjugation system is small to hardly change a color; and (2) the triphenyl amine skeleton has a high degree of freedom, and thus it is considered that color control is difficult because a band absorption becomes broad, and use of the triphenyl amine skeleton is extremely difficult particularly in color control of magenta where a width of absorption is restricted.

As a result of further studies performed by the present inventors based on the aforementioned finding, it has been found that use of a compound having an oxazine skeleton represented by the general formula (I) or the general formula (II) as an electrochromic compound can achieve electric durability that is the same level as electrical durability of a compound having a triphenyl amine skeleton, and favorably achieve various colors.

Examples of the halogen atom in the general formula (I) and the general formula (II) include a fluorine atom, a chlorine atom, a bromine atom, and an iodine atom.

Examples of the monovalent organic group in the general formula (I) and the general formula (II) include a hydroxyl group, a nitro group, a cyano group, a carboxyl group, a carbonyl group, an amide group, an aminocarbonyl group, a sulfonic acid group, a sulfonyl group, a sulfone amide group, an aminosulfonyl group, an amino group, an alkyl group, an alkenyl group, an alkynyl group, an aryl group, an alkoxy group, an aryloxy group, an alkylthio group, an arylthio group, and a heteroaryl group. The above-listed groups may have a substituent.

Examples of the groups that may have a substituent include: a carbonyl group that may have a substituent, such as an alkoxycarbonyl group that may have a substituent, an aryloxycarbonyl group that may have a substituent, an alkylcarbonyl group that may have a substituent, an arylcarbonyl group that may have a substituent, a monoalkylaminocarbonyl group that may have a substituent, a dialkylaminocarbonyl group that may have a substituent, a monoarylaminocarbonyl group that may have a substituent, and a diarylaminocarbonyl group that may have a substituent; a sulfonyl group that may have a substituent, such as an alkoxysulfonyl group that may have a substituent, an aryloxysulfonyl group that may have a substituent, an alkylsulfonyl group that may have a substituent, an arylsulfonyl group that may have a substituent, a sulfone amide group, a monoalkylaminosulfonyl group that may have a substituent, a dialkylaminosulfonyl group that may have a substituent, a monoarylaminosulfonyl group that may have a substituent, and a diarylaminosulfonyl group that may have a substituent; an alkylamino group, such as a monoalkylamino group that may have a substituent, a dialkylamino group that may have a substituent; an alkyl group that may have a substituent; an alkenyl group that may have a substituent; an alkynyl group that may have a substituent; an aryl group that may have a substituent; an alkoxy group that may have a substituent; an aryloxy group that may have a substituent; an alkylthio group that may have a substituent; an arylthio group that may have a substituent; and a heteroaryl group that may have a substituent.

Among the above-listed examples, an alkyl group having 1 or more carbon atoms, an alkenyl group having 2 or more carbon atoms, an alkynyl group having 2 or more carbon atoms, an aryl group having 6 or more carbon atoms, a heteroaryl group, an alkoxy group, an aryloxy group, and a heteroaryloxy group are preferable.

In view of readily availability of raw materials, the alkyl group having 1 or more carbon atoms is preferably a straight-chain, branched-chain, or cyclic alkyl group having 1 or more but 30 or less carbon atoms, and more preferably an alkyl group having 1 or more but 18 or less carbon atoms.

Examples of the alkyl group having 1 or more carbon atoms include a methyl group, an ethyl group, a propyl group, a butyl group, an isopropyl group, an isobutyl group, a pentyl group, a hexyl group, a heptyl group, an ethylhexyl group, an octyl group, a decyl group, a dodecyl group, a 2-butyloctyl group, an octadecyl group, a cyclopropyl group, a cyclobutyl group, a cyclopentyl group, a cyclohexyl group, and an adamantyl group.

Similar to the alkyl group having 1 or more carbon atoms, for example, the alkenyl group having 2 or more carbon atoms is preferably a straight-chain, branched-chain, or cyclic alkenyl group having 2 or more but 30 or less carbon atoms, and more preferably an alkenyl group having 2 or more but 18 or less carbon atoms.

The alkenyl group having 2 or more carbon atoms is a substituent that is the alkyl group having 1 or more carbon atoms from which any 2 hydrogen atoms have been removed. Examples of the alkenyl group having 2 or more carbon atoms include a vinyl group (ethenyl group), a propenyl group, a butenyl group, a pentenyl group, a hexenyl group, a heptanyl group, an octenyl group, a decenyl group, a dodecenyl group, an octadecenyl group, a cyclobutenyl group, a cyclopentenyl group, and a cyclohexcenyl group.

Similar to the alkyl group having 1 or more carbon atoms, for example, the alkynyl group having 2 or more carbon atoms is preferably a straight-chain, branched-chain, or cyclic alkenyl group having 2 or more but 30 or less carbon atoms, and more preferably an alkenyl group having 2 or more but 18 or less carbon atoms.

The alkynyl group having 2 or more carbon atoms is a substituent that is the alkyl group having 1 or more carbon atoms from which any 4 hydrogen atoms have been removed. Examples of the alkynyl group having 2 or more carbon atoms include an ethynyl group, a propynyl group, a butynyl group, a pentynyl group, a hexynyl group, a heptynyl group, an octynyl group, a decynyl group, a dodecynyl group, and an octadecynyl group.

For example, the aryl group having 6 or more carbon atoms is preferably an aryl group having 6 or more but 18 or less carbon atoms.

Examples of the aryl group having 6 or more carbon atoms include a phenyl group, an o-tolyl group, a m-tolyl group, a p-tolyl group, a p-chlorophenyl group, a p-fluorophenyl group, a p-trifluorophenyl group, a naphthyl group, a biphenyl group, an anthryl group, a phenanthryl group, and a pyrenyl group.

For example, the heteroaryl group is preferably a heteroaryl group having 2 or more but 12 or less carbon atoms.

Examples of constitutional elements of the heteroaryl group include a nitrogen atom, a sulfur atom, an oxygen atom, a silicon atom, and a selenium atom. Among the above-listed examples, the heteroaryl group preferably contains at least one selected from the group consisting of a nitrogen atom, a sulfur atom, and an oxygen atom.

Examples of the heteroaryl group include a monocyclic heteroaryl group and a polycyclic heteroaryl group.

Examples of the monocyclic heteroaryl group include a pyridine ring, a pyrimidine ring, a pyridazine ring, a pyrazine ring, tetrazine, a thiophene ring, a furan ring, pyrrole, imidazole, pyrazole, a thiazole ring, an oxazole ring, an isoxazole ring, an oxadiazole ring, a triazine ring, a tetrazole ring, and a triazole ring.

Examples of the polycyclic heteroaryl group include a quinoline group, an isoquinoline group, a quinazoline group, a phthalazine group, an indole group, a benzothiophene group, a benzofuran group, a benzoimidazole group, a benzothiadiazole group, an acridine group, a phenoxazine group, a phenothiazine group, a carbazole group, a benzodithiophene group, and a benzodifuran group.

In the general formula (I) and the general formula (II), the polymerizable functional group is not particularly limited, as long as the polymerizable functional group is a group that has a carbon-carbon double bond and is a polymerizable group. Examples of the polymerizable functional group include a 1-substituted ethylene functional group and a 1,1-substituted ethylene functional group.

(1) 1-Substituted Ethylene Functional Group

Examples of the 1-substituted ethylene functional group include functional groups represented by the following general formula (i).

[Chem.5]

  General formula (i)

In the general formula (i), $X_1$ is an arylene group that may have a substituent, an alkenylene group that may have a substituent, a group represented by —CO—, a group represented by —COO—, a group represented by —CON($R_{100}$)— [$R_{100}$ is a hydrogen atom, an alkyl group, an aralkyl group, or an aryl group], or a group represented by —S—.

Examples of the arylene group in the general formula (i) include a phenylene group that may have a substituent, and a naphthylene group.

Examples of the alkenylene group include an ethenylene group, a propenylene group, and a butenylene group.

Examples of the alkyl group include a methyl group and an ethyl group.

Examples of the aralkyl group include a benzyl group, a naphthylmethyl group, and a phenethyl group.

Examples of the aryl group include a phenyl group and a naphthyl group.

Specific examples of the polymerizable functional group represented by the general formula (i) include a vinyl group, a styryl group, a 2-methyl-1,3-butadienyl group, a vinylcarbonyl group, an acryloyl group, an acryloylamide group, and a vinyl thioether group.

(2) 1,1-Substituted Ethylene Functional Group

Examples of the 1,1-substituted ethylene functional group include functional groups represented by the following general formula (ii).

[Chem.6]

  General formula (ii)

In the general formula (ii), Y is an alkyl group that may have a substituent, an aralkyl group that may have a substituent, an aryl group that may have a substituent, a halogen atom, a cyano group, a nitro group, an alkoxy group, a group represented by —COOR$_{101}$ [$R_{101}$ is a hydrogen atom, an alkyl group that may have a substituent, an aralkyl group that may have a substituent, an aryl group that may have a substituent, or a group represented by CONR$_{102}$R$_{103}$ ($R_{102}$ and $R_{103}$ are each a hydrogen atom, an alkyl group that may have a substituent, an aralkyl group that may have a substituent, or an aryl group that may have a substituent, and $R_{102}$ and $R_{103}$ are identical or different)]. Moreover, $X_2$ is a substituent identical to $X_1$ in the general formula (i), a single bond, or an alkylene group, provided that at least one of Y and $X_2$ is an oxycarbonyl group, a cyano group, an alkenylene group, or an aromatic ring.

Examples of the aryl group of the general formula (ii) include a phenyl group and a naphtyl group.

Examples of the alkyl group include a methyl group and an ethyl group.

Examples of the alkoxy group include a methoxy group and an ethoxy group.

Examples of the aralkyl group include a benzyl group, a naphthylmethyl group, and a phenethyl group.

Specific examples of the polymerizable functional group represented by the general formula (ii) include an α-chlorinated acryloyloxy group, a methacryloyl group, an α-cyanoethylene group, an alpha-cyanoacryloyloxy group, an α-cyanophenylene group, and a methacryloylamino group.

Note that, examples of a substituent further substituting the substituents in $X_1$, $X_2$, and Y include a halogen atom, a nitro group, a cyano group, an alkyl group (e.g., a methyl group and an ethyl group), an alkoxy group (e.g., a methoxy group and an ethoxy group), an aryloxy group (e.g., a phenoxy group), an aryl group (e.g., a phenyl group and a naphthyl group), and an aralkyl group (e.g., a benzyl group and a phenethyl group).

Among the above-listed examples of the polymerizable functional group, an acryloyl group and a methacryloyl group are preferable.

In view of high resistance to oxidation and reduction, for example, the polymerizable functional group is preferably introduced as a substituent at a terminal of an alkyl group having 1 or more carbon atoms, an aryl group having 6 or more carbon atoms, or an aryl group substituted with an alkyl group having 7 or more carbon atoms. The polymerizable functional group is more preferably introduced as a substituent at a terminal of an alkyl group.

The polymerizable functional group is preferably bonded to a main skeleton via at least an alkyl group having 2 or more carbon atoms.

The monovalent organic group and the polymerizable functional group may be further substituted with a substituent.

Examples of the substituent of the monovalent organic group or the polymerizable functional group include a halogen atom, a nitro group, a cyano group, an alkyl group (e.g., a methyl group and an ethyl group), an alkoxy group (e.g., a methoxy group and an ethoxy group), an aryloxy group (e.g., a phenoxy group), an aryl group (e.g., a phenyl group and a naphthyl group), and an aralkyl group (e.g., a benzyl group and a phenethyl group).

Among the electrochromic compounds represented by the general formula (I) or the general formula (II), preferable are compounds in which a monovalent organic group of any of $R_1$ to $R_{13}$ is an alkyl group, an alkenyl group, an alkynyl group, an aryl group, a heteroaryl group, an alkoxy group, an aryloxy group, or a heteroaryloxy group.

Among the electrochromic compounds represented by the general formula (I) or the general formula (II), more preferable are compounds in which $R_3$ and $R_4$ are each a halogen atom, a monovalent organic group, or a polymerizable functional group.

In view of crystallinity and improved stability of an electrochromic compound that at least one of $R_3$ and $R_4$ is preferably a halogen atom, a monovalent organic group, or a polymerizable functional group because the halogen atom, the monovalent organic group, or the polymerizable functional group is introduced at a para position of the oxazine skeleton.

Specifically, the para position of the oxazine skeleton in the general formula (I) has a high electron density and high reactivity. It is highly possible that an expected side reaction, such as a dimerization reaction, a cyclization reaction, and a decomposition reaction, may be caused in oxidation and reduction states. The para position of the oxazine skeleton is preferably substituted with the halogen atom, the monovalent organic group, or the polymerizable functional group, other than a hydrogen atom.

Among the electrochromic compounds represented by the general formula (I) or the general formula (II), even more preferable are compounds in which the polymerizable functional group of any of $R_1$ to $R_{13}$ preferably contains an alkyl group, an aryl group, or an aryl group substituted with an alkyl group, with the polymerizable functional group of any of $R_1$ to $R_{13}$ being more preferably an acryloyl group or a methacryloyl group.

Specific examples of the electrochromic compound represented by the general formula (I) or (II) are listed below, but the electrochromic compound is not limited to the following compounds. In the structural formulae below, Me represents a methyl group.

[Chem.7]

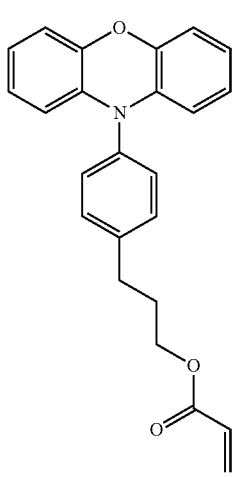

<Exemplary Compound 1>

[Chem.8]

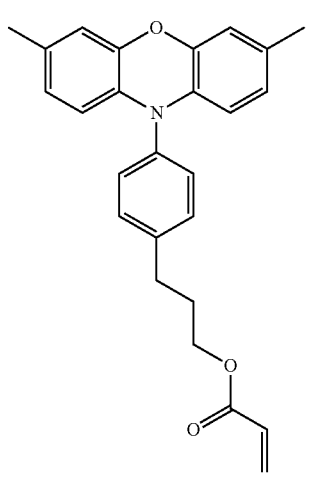

<Exemplary Compound 2>

[Chem.9]
<Exemplary Compound 3>
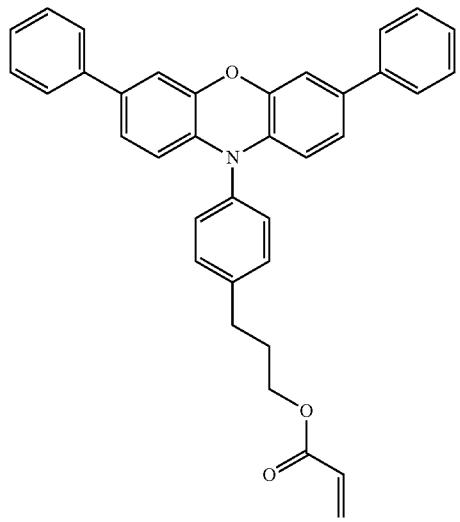
[Chem.10]
<Exemplary Compound 4>
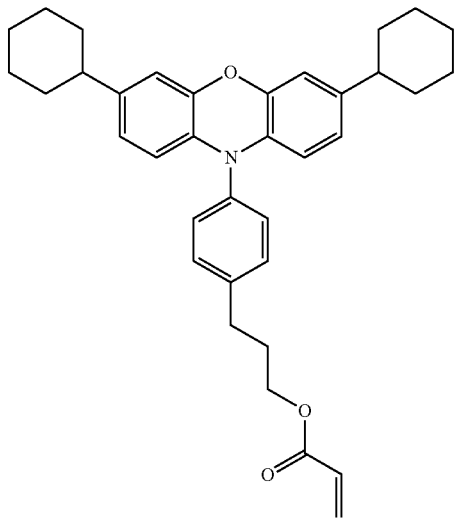
[Chem.11]
<Exemplary Compound 5>
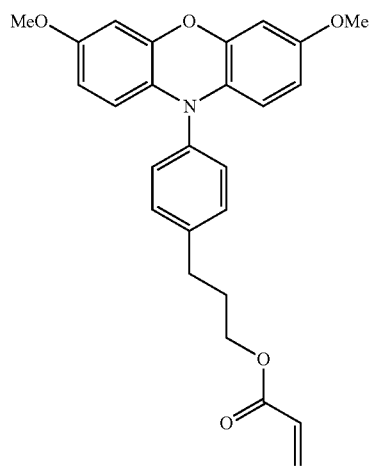
[Chem.12]
<Exemplary Compound 6>
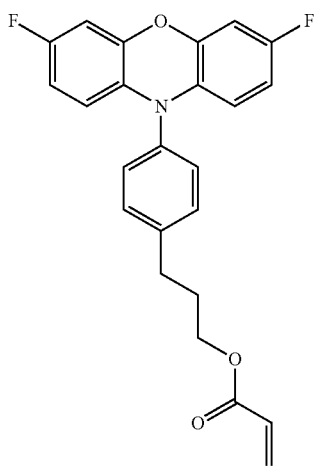
[Chem.13]
<Exemplary Compound 7>
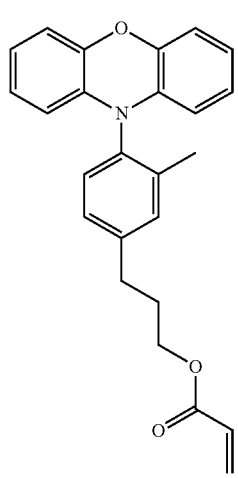
[Chem.14]
<Exemplary Compound 8>
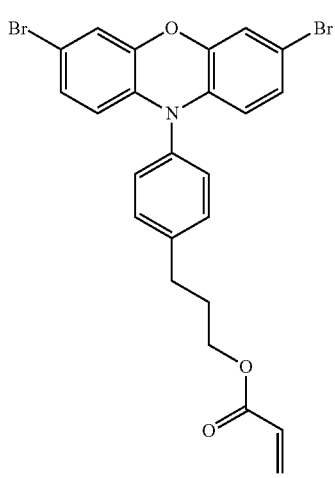

-continued
<Exemplary Compound 9>
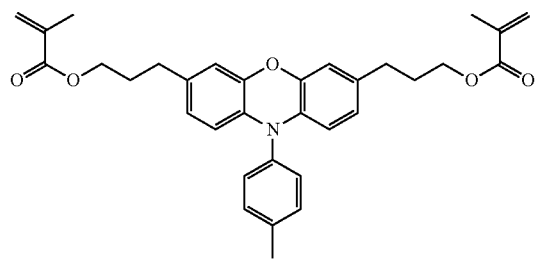
<Exemplary Compound 10>
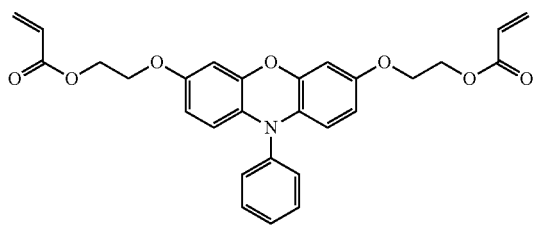
<Exemplary Compound 11>
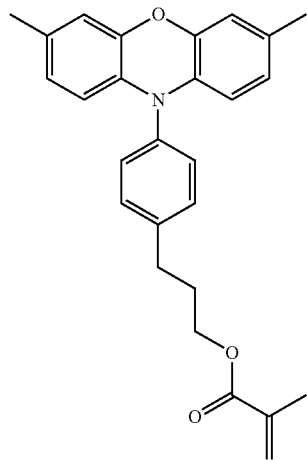
<Exemplary Compound 12>
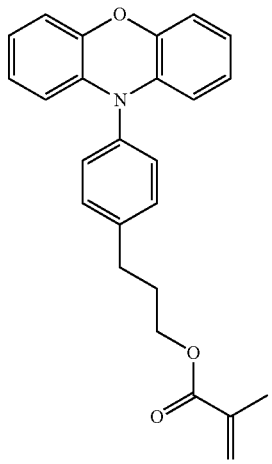
<Exemplary Compound 13>
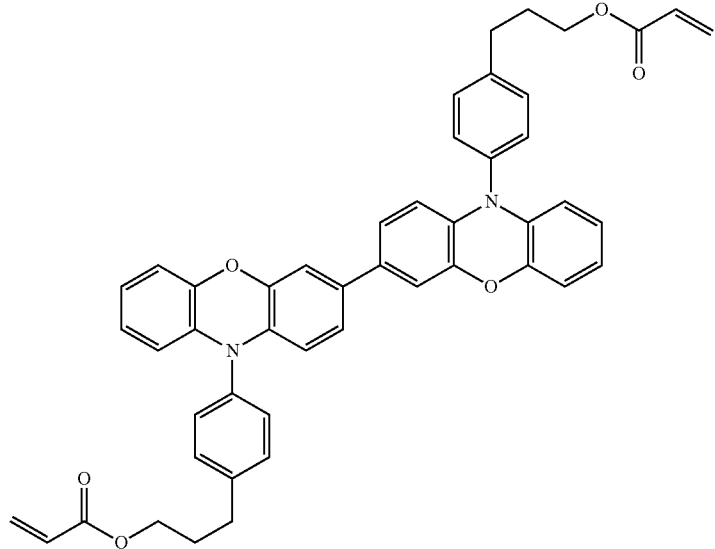

-continued

<Exemplary Compound 14>

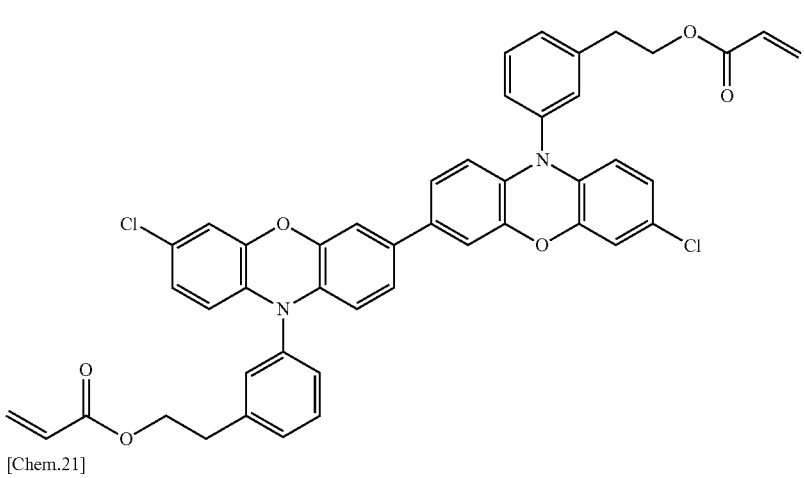

[Chem.20]

[Chem.21]

<Exemplary Compound 15>

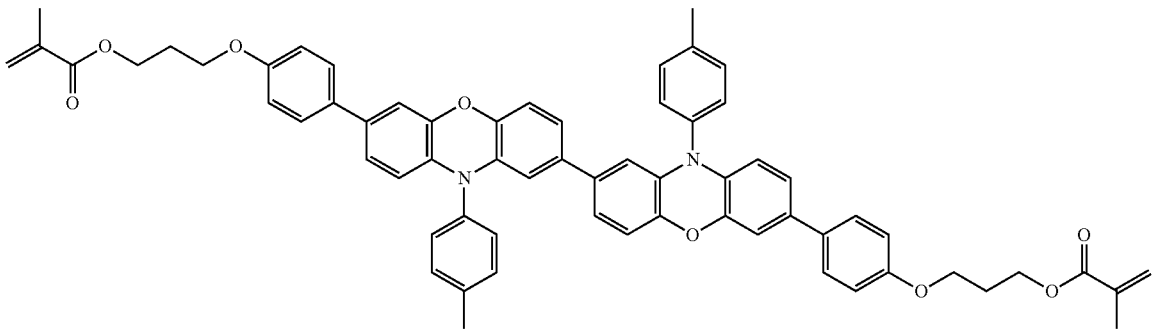

—Production Method—

The electrochromic compound represented by the general formula (I) or the general formula (II) can be obtained by successively performing a cross-coupling reaction between carbon-nitrogen using, for example, a phenyl compound represented by the general formula (III) in view of availability and toxicity of the compound, and for example, an amine compound represented by the general formula (IV) in the presence of a metal catalyst (e.g., a palladium catalyst, a nickel catalyst, and a copper catalyst) and an optional base, in an appropriate solvent.

[Chem.22]

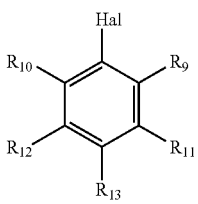

[General formula (III)]

In the general formula (III), $R_9$ to $R_{13}$ are identical to $R_9$ to $R_{13}$ in the general formula (I) and the general formula (II), and Hal is a halogen atom or a triflate group.

[Chem.23]

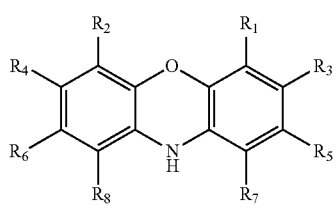

[General formula (IV)]

In the general formula (IV), $R_1$ to $R_8$ are identical to $R_1$ to $R_8$ in the general formula (I) and the general formula (II).

Examples of the halogen atom include a chlorine atom, a bromine atom, and an iodine atom. Among the above-listed examples, a chlorine atom and a bromine atom are preferable.

The base is not particularly limited and may be appropriately selected depending on the intended purpose. Examples of the base include strong bases.

Examples of the strong bases include sodium-tert-butoxide, potassium-tert-butoxide, potassium carbonate, cesium carbonate, and potassium phosphate.

The solvent is not particularly limited and may be appropriately selected depending on the intended purpose. Examples of the solvent include toluene, xylene, mesitylene, dioxane, tert-butyl alcohol, tetrahydrofuran, chlorobenzene, o-dichlorobenzene, nitrobenzene, and quinoline.

Examples of the catalyst include palladium acetate, trisbenzylidene acetone dipalladium, bisbenzylidene acetone palladium, copper, and copper oxide. The catalyst may be used in combination with an appropriate ligand.

Examples of the ligand include a phosphorus ligand (e.g., triphenylphosphine, tributylphosphine, and tri-tert-butylphosphine), and a nitrogen-based ligand (e.g., ethylene diamine, cyclohexyldiamine, phenanthroline, and bipyridyl).

Purification of a crude product of the electrochromic compound obtained after the reaction can be performed in accordance with any of various purification methods known in the art.

Examples of the purification method include solvent washing, recrystallization, column chromatography, reprecipitation, and sublimation purification.

(Electrochromic Composition)

An electrochromic composition of the present invention includes the electrochromic compound of the present invention, and another polymerizable compound different from the electrochromic compound. The electrochromic composition preferably includes a polymerization initiator, and may further include other ingredients, if necessary.

<Another Polymerizable Compound>

The another polymerizable compound is different from the electrochromic compound of the present invention, and is a compound containing at least one polymerizable functional group.

Examples of the another polymerizable compound include a monofunctional polymerizable compound, a bifunctional polymerizable compound, a tri- or higher functional polymerizable compound, a functional monomer, and a polymerizable oligomer. Among the above-listed compounds, a bifunctional polymerizable compound is particularly preferable.

The at least one polymerizable functional groups in the another polymerizable compound is the same as the polymerizable functional groups of the electrochromic compound of the present invention. Among the above-listed polymerizable functional groups, an acryloyl group and a methacryloyl group are particularly preferable.

Examples of the monofunctional polymerizable compound include 2-(2-ethoxyethoxy)ethylacrylate, methoxy polyethylene glycol monoacrylate, methoxy polyethylene glycol monomethacrylate, phenoxy polyethylene glycol acrylate, 2-acryloyloxyethyl succinate, 2-ethylhexyl acrylate, 2-hydroxyethyl acrylate, 2-hydroxypropyl acrylate, tetrahydrofurfuryl acrylate, 2-ethylhexylcarbitol acrylate, 3-methoxybutyl acrylate, benzyl acrylate, cyclohexyl acrylate, isoamyl acrylate, isobutyl acrylate, methoxytriethylene glycol acrylate, phenoxytetraethylene glycol acrylate, cetyl acrylate, isostearyl acrylate, stearyl acrylate, and styrene monomers. These monofunctional polymerizable compounds may be used alone or in combination.

Examples of the bifunctional polymerizable compound include 1,3-butanediol diacrylate, 1,4-butanediol diacrylate, 1,4-butanediol dimethacrylate, 1,6-hexanediol diacrylate, 1,6-hexanediol dimethacrylate, diethylene glycol diacrylate, polyethylene glycol diacrylate, neopentyl glycol diacrylate, EO-modified bisphenol A diacrylate, EO-modified bisphenol F diacrylate, and neopentyl glycol diacrylate. These compounds may be used alone or in combination.

Examples of the tri- or higher functional polymerizable compound include trimethylolpropane triacrylate (TMPTA), trimethylolpropane trimethacrylate, EO-modified trimethylolpropane triacrylate, PO-modified trimethylolpropane triacrylate, caprolactone-modified trimethylolpropane triacrylate, HPA-modified trimethylolpropane trimethacrylate, pentaerythritol triacrylate, pentaerythritol tetraacrylate (PETTA), glycerol triacrylate, ECH-modified glycerol triacrylate, EO-modified glycerol triacrylate, PO-modified glycerol triacrylate, tris(acryloxyethyl) isocyanurate, dipentaerythritol hexacrylate (DPHA), caprolactone-modified dipentaerythritol hexacrylate, dipentaerythritol hydroxyl pentacrylate, alkyl-modified dipentaerythritol pentacrylate, alkyl-modified dipentaerythritol tetracrylate, alkyl-modified dipentaerythritol triacrylate, dimethylolpropane tetraacrylate (DTMPTA), pentaerythritol ethoxytetracrylate, EO-modified phosphoric acid triacrylate, and 2,2,5,5-tetrahydroxymethylcyclopentanone tetraacrylate. These compounds may be used alone or in combination.

In the above, "EO-modified" denotes ethylene oxy-modified, and "PO-modified" denotes propylene oxy-modified.

Examples of the functional monomer include: monomers substituted with a fluorine atom, such as octafluoropentyl acrylate, 2-perfluorooctylethyl acrylate, 2-perfluorooctylethyl methacrylate, and 2-perfluoroisononylethyl acrylate; vinyl monomers having a polysiloxane group disclosed in Japanese Examined Patent Publication Nos. 05-60503 and 06-45770, such as acryloyl polydimethylsiloxane ethyl, methacryloyl polydimethylsiloxane ethyl, acryloyl polydimethylsiloxane propyl, acryloyl polydimethylsiloxane butyl, and diacryloyl polydimethylsiloxane diethyl, each of which contains from 20 through 70 siloxane repeating units; and acrylates and methacrylates. These monomers may be used alone or in combination.

Examples of the polymerizable oligomer include epoxy acrylate-based oligomers, urethane acrylate-based oligomers, and polyester acrylate-based oligomers.

At least one of the electrochromic compound of the present invention and the another polymerizable compound different from the electrochromic compound of the present invention is preferably has two or more polymerizable functional groups in view of formation of a cross-linked structure.

An amount of the electrochromic compound of the present invention is preferably 10% by mass or greater but 100% by mass or less, and more preferably 30% by mass or greater but 90% by mass or less, relative to a total amount of the electrochromic composition.

When the amount of the electrochromic compound is 10% by mass or greater, an electrochromic function of an electrochromic layer can be sufficiently exhibited, and a resultant element has excellent durability to repetitive use with application of voltage, and has excellent coloring sensitivity.

An electrochromic function of the electrochromic layer can be also exhibited when the amount of the electrochromic compound is 100% by mass. In this case, coloring sensitivity is the highest with respect to the thickness. In contrast, compatibility to an ionic liquid required for exchanging electric charges may become low. Therefore, electric properties may be deteriorated due to reduction in durability caused by repetitive use with application of voltage. The amount of the electrochromic compound for use cannot be flatly determined because electric properties required are different depending on a process for use, but the amount of the electrochromic compound is more preferably 30% by mass or greater but 90% by mass or less in view of a balance between coloring sensitivity and durability to repetitive use.

<Polymerization Initiator>

The electrochromic composition preferably includes a polymerization initiator, if necessary, in order to efficiently perform a polymerization/cross-linking reaction between the electrochromic compound of the present invention and the another polymerizable compound different from the electrochromic compound of the present invention.

Examples of the polymerization initiator include a thermal polymerization initiator and a photopolymerization initiator. Among the above-listed examples, a photopolymerization initiator is preferable in view of efficiency of polymerization.

The thermal polymerization initiator is not particularly limited and may be appropriately selected depending on the intended purpose. Examples of the thermal polymerization initiator include: peroxide-based initiators, such as 2,5-dimethylhexane-2,5-dihydroperoxide, dicumyl peroxide, benzoyl peroxide, t-butylcumyl peroxide, 2,5-dimethyl-2,5-di(peroxybenzoyl)hexyne-3, di-t-butylperoxide, t-butylhydroperoxide, cumene hydroperoxide, and lauroyl peroxide; and azo-initiators, such as azobisisobutyl nitrile, azobiscyclohexane carbonitrile, methyl azobisisobutyrate, azobisisobutylamidine hydrochloride, and 4,4'-azobis-4-cyanovaleric acid. These thermal polymerization initiators may be used alone or in combination.

The photopolymerization initiator is not particularly limited and may be appropriately selected depending on the intended purpose. Examples of the photopolymerization initiator include: acetophenone-based or ketal-based photopolymerization initiators, such as diethoxyacetophenone, 2,2-dimethoxy-1,2-diphenylethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1, 2-hydroxy-2-methyl-1-phenylpropan-1-one, 2-methyl-2-morpholino(4-methylthiophenyl)propan-1-one, and 1-phenyl-1,2-propanedione-2-(o-ethoxycarbonyl)oxime; benzoin ether-based photopolymerization initiators, such as benzoin, benzoin methyl ether, benzoin ethyl ether, benzoin isobutyl ether, and benzoin isopropyl ether; benzophenone-based photopolymerization initiators, such as benzophenone, 4-hydroxybenzophenone, methyl obenzoylbenzoate, 2-benzoylnaphthalene, 4-benzoylbiphenyl, 4-benzoylphenyl ether, acrylated benzophenone, and 1,4-benzoylbenzene; and thioxanthone-based photopolymerization initiators, such as 2-isopropylthioxanthone, 2-chlorothioxanthone, 2,4-dimethylthioxanthone, 2,4-diethylthioxanthone, and 2,4-dichlorothioxanthone. These photopolymerization initiators may be used alone or in combination.

Other examples of the photopolymerization initiator include ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-trimethylpentylphosphine oxide, methylphenyl-glyoxylic ester, 9,10-phenanthrene, acridine-based compounds, triazine-based compounds, and imidazole-based compounds.

Note that, a compound having a photopolymerization acceleration effect may be used alone or in combination with the photopolymerization initiator. Examples of such a compound include triethanol amine, methyldiethanol amine, ethyl 4-dimethylaminobenzoate, isoamyl 4-dimethylaminobenzoate, ethyl (2-dimethylamino)benzoate, and 4,4'-dimethylaminobenzophenone.

An amount of the polymerization initiator is preferably 0.5 parts by mass or greater but 40 parts by mass or less, and more preferably 1 part by mass or greater but 20 parts by mass or less, relative to 100 parts by mass of a total amount of the polymerizable compound.

<Other Ingredients>

The other ingredients are not particularly limited and may be appropriately selected depending on the intended purpose. Examples of the other ingredients include bearing particles, filler, a solvent, a plasticizer, a leveling agent, a sensitizer, a dispersing agent, a surfactant, and an antioxidant.

—Bearing Particles—

In a case where the electrochromic compound is combined with another electrochromic material, bearing particles can be used. In a case where an electrochromic compound, other than the electrochromic compound of the present invention, has a phosphonic acid group, a sulfonic acid group, a phosphoric acid group, or a carboxyl group as a bonding or adsorption structure, for example, the electrochromic compound easily forms a complex with the nanostructure to thereby form an electrochromic composition having excellent color image retainability. Two or more of the phosphonic acid groups, the sulfonic acid groups, the phosphoric acid groups and the carboxyl groups may be contained in the electrochromic compound. In a case where the electrochromic compound of the present invention contains a silyl group or a silanol group, the electrochromic compound is bonded to the nanostructure via a siloxane bond, which is a strong bond. Accordingly, a stable electrochromic composition is obtained. The siloxane bond is a chemical bond via a silicon atom and an oxygen atom. Moreover, a bonding method or manner in the electrochromic composition is not particularly limited, as long as the electrochromic composition has a structure where the electrochromic compound and the nanostructure are bonded via a siloxane bond.

The conductive nanostructure or semiconductive nanostructure is a structure having irregularities of nanoscale, such as nanoparticles, and a nanoporous structure.

For example, a material for constituting the conductive nanostructure or semiconductive nanostructure is preferably a metal oxide in view of transparency and conductivity.

Examples of the metal oxide include titanium oxide, zinc oxide, tin oxide, zirconium oxide, cerium oxide, yttrium oxide, boron oxide, magnesium oxide, strontium titanate, potassium titanate, barium titanate, calcium titanate, calcium oxide, ferrite, hafnium oxide, tungsten oxide, iron oxide, copper oxide, nickel oxide, cobalt oxide, barium oxide, strontium oxide, vanadium oxide, aluminosilicic acid, calcium phosphate, and aluminosilicate. These metal oxides may be used alone or in combination. Among the above-listed metal oxides, titanium oxide, zinc oxide, tin oxide, zirconium oxide, iron oxide, magnesium oxide, indium oxide, and tungsten oxide are preferable, and titanium oxide is more preferable, in view of electric properties such as electroconductivity, or physical properties such as optical characteristics.

A shape of the metal oxide is preferably particles having an average primary particle diameter of 30 nm or smaller. As the average primary particle diameter of the metal oxide is smaller, transmittance of the metal oxide to light is increased more. Accordingly, the shape having a large surface area per unit volume (referred to as "specific surface area" hereinafter) is used. Because the nanostructure has a large specific surface area, the electrochromic compound is more efficiently born on the nanostructure, leading to an electrochromic element that realizes excellent coloring-decoloring display contrast ratio, and excellent multi-color display. The specific surface area of the nanostructure is not particularly limited and may be appropriately selected depending on the intended purpose, but the specific surface area is preferably 100 $m^2$/g or greater.

—Filler—

The filler is not particularly limited and may be appropriately selected depending on the intended purpose. Examples of the filler include organic filler and inorganic filler.

Examples of the inorganic filler include: metal powders, such as copper, tin, aluminium, and indium; metal oxides, such as silicon oxide (silica), tin oxide, zinc oxide, titanium oxide, aluminium oxide (alumina), zirconium oxide, indium oxide, antimony oxide, bismuth oxide, calcium oxide, antimony-doped tin oxide (ATO), and tin-doped indium oxide; and metal fluorides, such as tin fluoride, calcium fluoride, and aluminium fluoride. The above-listed examples of the inorganic filler may be used alone or in combination. Among the above-listed examples, metal oxides are preferable, and silica, alumina, and antimony-doped tin oxide (ATO) are particularly preferable in view of transparency, stability and easiness of a surface treatment.

Examples of the organic filler include: resins, such as polyester, polyether, polysulfide, polyolefin, silicone, and polytetrafluoroethylene; low-molecular-weight compounds, such as fatty acid; and pigments, such as phthalocyanine. The above-listed examples of the organic filler may be used alone or in combination. Among the above-listed examples, resins are preferable in view of transparency and insolubility.

An average primary particle diameter of the filler is preferably 1 μm or smaller, and more preferably 10 nm or greater but 1 μm or smaller. When the average primary particle diameter of the filler is 1 μm or smaller, coarse particles are not present, a surface state of an obtained film is excellent, and excellent surface smoothness is obtained.

An amount of the filler based on a solid content is preferably 0.3 parts by mass or greater but 1.5 parts by mass or less, and more preferably 0.6 parts by mass or greater but 0.9 parts by mass or less, relative to 100 parts by mass of a total amount of the polymerizable compound.

When the amount of the filler is 0.3 parts by mass or greater, an effect obtainable by adding the filler is sufficiently exhibited, and excellent film formability can be achieved. When the amount of the filler is 1.5 parts by mass or smaller, excellent electrochemical properties of a produced electrochromic display element can be obtained.

The electrochromic compound and the electrochromic composition of the present invention can be suitably used for various applications, such as electrochromic display elements, large-scale display boards (e.g., display boards for stock prices), anti-glare mirrors, dimming elements (e.g., dimming glass), low-voltage-driven elements (e.g., key switches according to the touch panel system), optical switches, optical memories, electronic paper, and electronic album. Among the above-listed examples, electrochromic display elements are particularly preferable.

(Electrochromic Display Element)

An electrochromic display element of the present invention includes a first electrode, a second electrode, and an electrolyte disposed between the first electrode and the second electrode. The electrochromic display element may further include other members, if necessary.

The first electrode contains the electrochromic compound of the present invention or the electrochromic composition of the present invention.

The phrase "the first electrode contains the electrochromic compound of the present invention or the electrochromic composition of the present invention" includes an embodiment where an electrochromic layer containing the electrochromic compound or the electrochromic composition is laminated on the first electrode, an embodiment where two or more layers of the electrochromic layers are laminated on the first electrode, and an embodiment where the electrochromic layer is laminated on part of the first electrode.

—First Electrode and Second Electrode—

Examples of a material constituting the first electrode and a material constituting the second electrode include transparent conductive substrates. For example, the transparent conductive substrate is preferably glass or a plastic film, which is coated with a transparent conductive film.

A material of the transparent conductive film is not particularly limited and may be appropriately selected depending on the intended purpose, as long as the material is a transparent material having conductivity. Examples of the material include inorganic materials, such as tin-doped indium oxide (may be referred to as "ITO" hereinafter), fluorine-doped tin oxide (may be referred to as "FTO" hereinafter), antimony-doped tin oxide (may be referred to as "ATO" hereinafter), and zinc oxide. Among the above-listed materials, InSnO, GaZnO, SnO, $In_2O_3$, and ZnO are preferable.

Moreover, it is also possible to use an electrode which is prepared by forming transparent carbon nanotubes, or a highly-conductive non-transparent material, such as Au, Ag, Pt, and Cu, into a fine network, to improve conductivity with maintaining transparency.

An average thickness of each of the first electrode and the second electrode is adjusted to obtain an electric resistance value required for an oxidation-reduction reaction of an electrochromic layer.

When ITO is used as materials of the first electrode and the second electrode, for example, an average thickness of each of the first electrode and the second electrode is preferably 50 nm or greater but 500 nm or less.

Examples of a production method of each of the first electrode and the second electrode include vacuum vapor deposition, sputtering, and ion plating.

A coating method of a material of each of the first electrode and the second electrode is not particularly limited as long as the method can coat the material. Examples of the coating method include spin coating, casting, microgravure coating, gravure coating, bar coating, roll coating, wire bar coating, dip coating, slit coating, capillary coating, spray coating, nozzle coating, and various printing methods, such as gravure printing, screen printing, flexographic printing, offset printing, reverse printing, and inkjet printing.

—Electrolyte—

The electrolyte is disposed between the first electrode and the second electrode.

Examples of the electrolyte include inorganic ionic salts (e.g., alkali metal salts and alkaline earth metal salts), quaternary ammonium salts, and supporting electrolytes, such as acids and bases. Specific examples include $LiClO_4$, $LiBF_4$, $LiAsF_6$, $LiPF_6$, $LiCF_3SO_3$, $LiCF_3COO$, $KCl$, $NaClO_3$, $NaCl$, $NaBF_4$, $NaSCN$, $KBF_4$, $Mg(ClO_4)_2$, and $Mg(BF_4)_2$. These electrolytes may be used alone or in combination.

An ionic liquid may be used as a material of the electrolyte. Among ionic liquids, organic ionic liquids are preferably used because each organic ionic liquid has a molecular structure which exists as a liquid in a wide temperature range including room temperature.

Examples of a cationic component of the molecular structure which exists as a liquid in a wide temperature range including room temperature include: imidazole derivatives, such as N,N-dimethylimidazole salt, N,N-methylethylimidazole salt, and N,N-methylpropylimidazole salt; pyridinium derivatives, such as N,N-dimethylpyridinium salt and N,N-methylpropylpyridinium salt; and aliphatic quaternary ammonium salts, such as trimethylpropyl ammonium salt, trimethylhexyl ammonium salt, and triethylhexyl ammonium salt. As an anionic component of the molecular structure, a compound containing fluorine is preferably used in view of stability in the atmosphere. Examples of the anionic component include $BF_4^-$, $CF_3SO_3^-$, $PF_4^-$, and $(CF_3SO_2)_2N^-$. The above-listed examples may be used alone or in combination.

A material of the electrolyte is preferably an ionic liquid prepared with an any combination of the cationic component and the anionic component.

The ionic liquid may be directly dissolved in a photopolymerizable monomer, oligomer, or liquid crystal material. In a case where solubility is poor, a solution prepared by dissolving the ionic liquid in a small amount of a solvent may be blended with a photopolymerizable monomer, oligomer, or liquid crystal material.

Examples of the solvent include propylene carbonate, acetonitrile, gamma-butyrolactone, ethylene carbonate, sulfolane, dioxolane, tetrahydrofuran, 2-methyltetrahydrofuran, dimethylsulfoxide, 1,2-dimethoxyethane, 1,2-ethoxymethoxyethane, polyethylene glycol, and alcohols. These solvents may be used alone or in combination.

The electrolyte is not necessarily a low-viscous liquid, and can be in a various state, such as a gel, a cross-linked polymer, or a liquid crystal dispersion. It is advantageous to form the electrolyte into a gel or solid state in view of an improvement in strength of a resultant element, and an improvement in reliability of the element.

A solidification method is preferably to retain the electrolyte and the solvent in a polymer because high ion conductivity and a solid strength can be obtained.

The polymer is preferably a photocurable resin because an element can be produced at a low temperature and within a short period compared to a method where a thin film is formed through thermal polymerization or by evaporating a solvent.

An average thickness of an electrolyte layer formed of the electrolyte is not particularly limited and may be appropriately selected depending on the intended purpose, but the average thickness is preferably 100 nm or greater but 100 µm or less.

The electrochromic layer is not particularly limited and may be appropriately selected depending on the intended purpose. The electrochromic layer can be suitably formed by a method where a coating liquid prepared by dispersing or dissolving the electrochromic compound of the present invention in a solvent is applied onto a surface of the first electrode, a method where the electrochromic composition of the present invention is born on the conductive or semiconductive nanostructure, or a below-described production method of an electrochromic display element.

An average thickness of the electrochromic layer is preferably 0.1 µm or greater but 30 µm or less, and more preferably 0.4 µm or greater but 10 µm or less.

—Other Members—

The other members are not particularly limited and may be appropriately selected depending on the intended purpose. Examples of the other members include a support, an insulating porous layer, an antideterioration layer, and a protective layer.

—Support—

As the support, any of organic materials or inorganic material known in the art can be used as it is, as long as the material is a transparent material that can support layers.

Examples of the support include: a glass substrate, such as non-alkali glass, borosilicate glass, float glass, and soda-line glass; and a resin substrate, such as a polycarbonate resin, an acrylic resin, polyethylene, polyvinyl chloride, polyester, an epoxy resin, a melamine resin, a phenol resin, a polyurethane resin, and a polyimide resin.

A surface of the support may be coated with a transparent insulating layer, a UV-cut layer, or an antireflection layer in order to enhance water-vapor barrier properties, gas barrier properties, ultraviolet ray resistance and visibility.

A shape of the support is not particularly limited and may be appropriately selected depending on the intended purpose. The shape may be a rectangle or a circle.

Two or more of the supports may be laminated. For example, the support having a structure where the electrochromic display element is sandwiched between two glass substrates can enhance water-vapor barrier properties and gas barrier properties.

—Insulating Porous Layer—

The insulating porous layer has a function of retaining the electrolyte, as well as separating the first electrode and the second electrode from each other to attain electrical insulation between the first electrode and the second electrode.

A material of the insulating porous layer is not particularly limited as long as the material is porous. The material is preferably an organic material, an inorganic material, or a composite of the organic material and the inorganic material, all of which have high insulating properties and durability and excellent film formability.

Examples of a formation method of the insulating porous layer include a sintering method (a method where polymer particles or inorganic particles are added to a binder to partially fuse the particles to utilize pores generated between the particles), an extraction method (a method where, after forming a constituting layer with an organic or inorganic material soluble in a solvent and a binder insoluble in the solvent, the organic or inorganic material is dissolved with the solvent to obtain pores), a foaming method where a coating liquid is foamed, a phase transformation method where a mixture of high-molecular-weight compounds are phase-separated by appropriately using a good solvent and a poor solvent, and a radiation method where pores are formed by applying various radial rays.

—Antideterioration Layer—

The antideterioration layer causes a reverse chemical reaction to a reaction of an electrochromic layer formed of the electrochromic composition to take a balance of charges. In this manner, it is possible to prevent corrosions or deteriorations caused by an irreversible oxidation or reduction reaction of the first electrode and the second electrode. Note that, the reverse chemical reaction means functioning as a capacitor as well as a case where the antideterioration layer is oxidized or reduced.

A material of the antideterioration layer is not particularly limited and may be appropriately selected depending on the intended purpose, as long as the material is a material that prevents corrosions caused by an irreversible oxidation or reduction reaction of the first electrode and the second electrode. For example, antimony tin oxide, nickel oxide, titanium oxide, zinc oxide, tin oxide, or conductive or semiconductive metal oxide containing two or more of the above-listed materials can be used.

The antideterioration layer can be composed of a porous film that has a degree of porosity not to interfere an injection of the electrolyte. For example, a preferable porous film that permeates the electrolyte and functions as an antideterioration layer can be obtained by fixing conductive or semiconductive metal oxide particles (e.g., antimony tin oxide, nickel oxide, titanium oxide, zinc oxide, and tin oxide) on the second electrode with a binder (e.g., an acryl-based binder, an alkyd-based binder, an isocyanate-based binder, an urethane-based binder, an epoxy-based binder, and a phenol-based binder).

Use of a conductive or semiconudctive nanostructure identical to that constituting the electrochromic composition as the antideterioration layer is preferable because a production process of the first electrode and the electrochromic composition, and a production process of the second electrode and the antideterioration layer can be partially unified.

—Protective Layer—

The protective layer can protect the electrochromic display element from external stress and chemicals used in washing processes. Moreover, the protective layer can prevent leakage of the electrolyte and migration of substances (e.g., moisture and oxygen in the air) that are unnecessary for stable operations of the electrochromic display element.

An average thickness of the protective layer is not particularly limited and may be appropriately selected depending on the intended purpose. The average thickness of the protective layer is preferably 1 μm or greater but 200 μm or less.

Examples of a material of the protective layer include UV-ray curable resins and thermosetting resins. Specific examples of the material include acryl-based resins, urethane-based resins, and epoxy-based resins.

<Production Method of Electrochromic Display Element>

The production method of an electrochromic display element is a production method of an electrochromic display element that includes a first electrode, a second electrode, and an electrolyte disposed between the first electrode and the second electrode. The production method includes a coating step, preferably includes a cross-linking step, and may further include other steps, if necessary.

—Coating Step—

The coating step includes coating an electrochromic composition onto the first electrode, where the electrochromic composition includes the electrochromic compound of the present invention and another polymerizable compound different from the electrochromic compound of the present invention.

As the electrochromic compound of the present invention and another polymerizable compound different from the electrochromic compound of the present invention, those described in the descriptions of the electrochromic display element can be used.

A coating liquid containing the electrochromic compound of the present invention and another polymerizable compound different from the electrochromic compound of the present invention is coated. The coating liquid is optionally diluted with a solvent before coating.

The solvent is not particularly limited and may be appropriately selected depending on the intended purpose. Examples of the solvent include: alcohol-based solvents, such as methanol, ethanol, propanol, and butanol; ketone-based solvents, such as acetone, methyl ethyl ketone, methyl isobutyl ketone, and cyclohexanone; ester-based solvents, such as ethyl acetate, and butyl acetate; ether-based solvents, such as tetrahydrofuran, dioxane, and propyl ether; halogen-based solvents, such as dichloromethane, dichloroethane, trichloroethane, and chlorobenzene; aromatic solvents, such as benzene, toluene, and xylene; and cellosolve-based solvents, such as methylcellosolve, ethylcellosolve, and cellosolve acetate. These solvents may be used alone or in combination.

Note that, a diluting ratio with the solvent varies depending on solubility of a composition, a coating method, and an intended thickness of a target electrochromic layer, and the diluting ratio is appropriately selected.

The coating can be performed, for example, by dip coating, spray coating, bead coating, and ring coating.

—Cross-Linking Step—

The cross-linking step includes applying heat or optical energy to the applied electrochromic composition to cross-link the electrochromic composition.

After coating the electrochromic composition onto the first electrode, energy is externally applied to the electrochromic composition to cure the electrochromic composition, to thereby form an electrochromic layer. Examples of the external energy include heat, light, and radial rays. A method for applying the heat energy is performed by heating from a side of the coated surface or a side of the support using gas (e.g., air and nitrogen), vapor, various heat media, infrared rays, or electromagnetic waves. The heating temperature is not particularly limited and may be appropriately selected depending on the intended purpose. The heating temperature is preferably 60° C. or higher but 170° C. or lower.

As the light energy, UV irradiation light sources mainly having emission wavelength in ultraviolet rays (UV), such as high-pressure mercury lamps, and metal halide lamps can be used. However, it is possible to use a visible light source matched to an absorption wavelength of the polymerizable compound or the photopolymerization initiator.

A radiation dose of UV is not particularly limited and may be appropriately selected depending on the intended purpose. The radiation dose is preferable 5 mW/cm$^2$ or greater but 15,000 mW/cm$^2$ or less.

—Other Steps—

Examples of the other steps include a first-electrode forming step, a second-electrode forming step, an insulating-porous layer forming step, an antideterioration-layer forming step, a protective-layer forming step, and a bonding step.

FIG. 1 is a schematic view illustrating one example of the electrochromic display element of the present invention. As illustrated in FIG. 1, the electrochromic display element 8 containing a first electrode 1, a second electrode 2 disposed to face the first electrode 1 with a space between the first electrode 1 and the second electrode 2, and an electrolyte 3 disposed between the first electrode 1 and the second electrode 2, where an electrochromic compound 4 is dissolved in the electrolyte 3. In the electrochromic display element, the electrochromic compound 4 colors and decolors only at surfaces of the electrodes as a result of oxidation and reduction reactions.

FIG. 2 is a schematic view illustrating another example of the electrochromic display element of the present invention. As illustrated in FIG. 2, the electrochromic display element 18 contains a first electrode 10, a second electrode 12 disposed to face the first electrode 10 with a space between the first electrode 10 and the second electrode 12, an electrolyte 13 disposed between the first electrode 10 and the second electrode, and a display layer 15 containing the electrochromic composition 14a disposed at a surface of the first electrode 10.

An electrochromic compound in the electrochromic composition includes a polymerizable functional group in a molecular structure of the electrochromic compound, and the electrochromic compound is bonded to a conductive or semiconductive nanostructure using the polymerizable functional group as a binding group, to thereby constitute the electrochromic composition. The electrochromic composition 14a is arranged into a layer on the first electrode 10, to thereby form the display layer 15.

FIG. 3 is a schematic view illustrating another example of the electrochromic display element of the present invention. As illustrated in FIG. 3, the electrochromic display element 28 contains a first electrode 20, a second electrode 22 disposed to face the first electrode 20 with a space between the first electrode 20 and the second electrode 22, an electrolyte 23 disposed between the first electrode 20 and the second electrode 22, and a display layer 25 containing the electrochromic composition 24a disposed at a surface of the first electrode 20. Moreover, a white reflection layer 26 composed of white particles is disposed at a side of the second electrode 22 facing the first electrode.

EXAMPLES

The present invention will next be described by way of Examples, but the present invention should not be construed as being limited to these Examples.

In each of the following examples, an intermediate product generated at the first step from raw materials is referred to as Intermediate Product X-Y (X denotes the number of Example, and Y denotes the number of step). Note that, a final product is not presented in the aforementioned manner because the final product is not an intermediate product.

Example 1

<Synthesis of Electrochromic Compound 1>

Electrochromic Compound 1 was synthesized according to the following scheme.

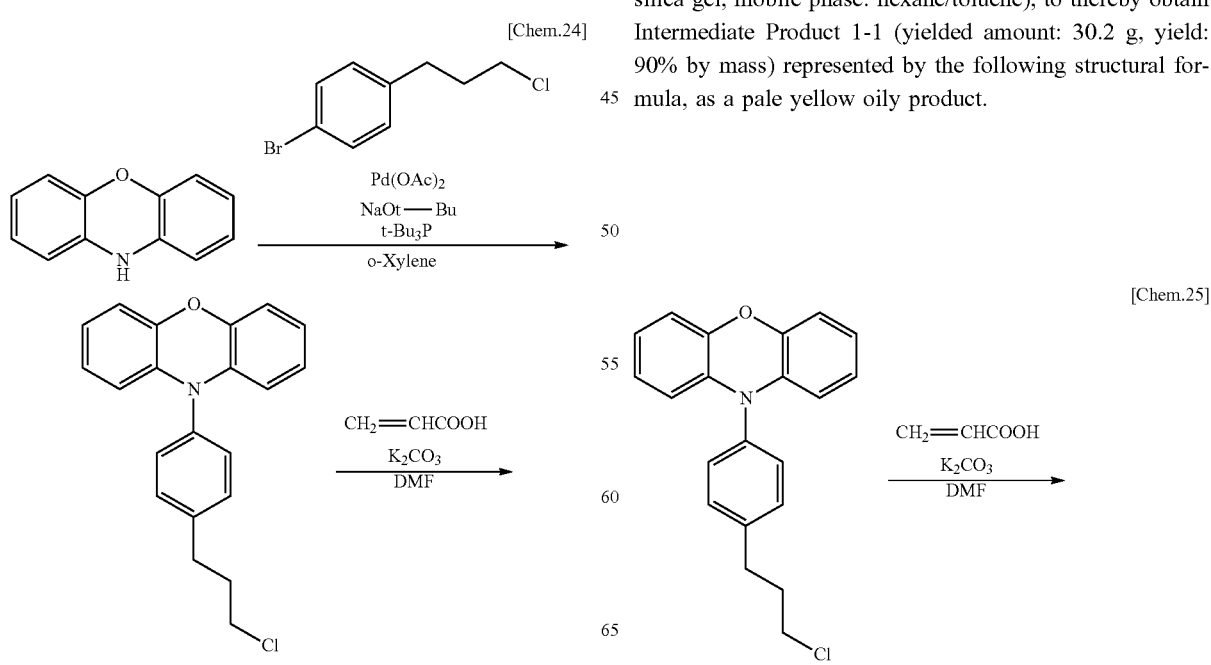

[Chem.24]

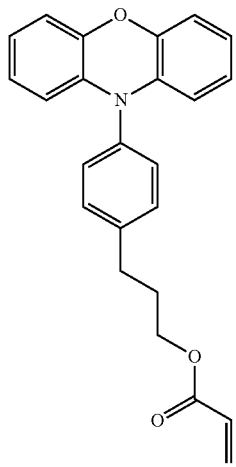

—Synthesis of Intermediate Product 1-1—

A flask purged with nitrogen was charged with phenoxazine (18.3 g, 100 mmol), 1-bromo-4-(3-chloropropyl)benzene (23.4 g, 100 mmol), palladium acetate (225 mg, 1.0 mmol), t-butoxysodium (14.4 g, 150 mmol), and o-xylene (420 mL). The resultant solution was subjected to bubbling with argon gas, followed by adding tetrakistrit-butylphosphine (624 mg, 3.08 mmol). The resultant mixture was heated and stirred for 2 hours at 115° C. The resultant reaction solution was cooled to room temperature, followed by CELITE filtration. Subsequently, the separated organic phase was concentrated, and the residue was purified by silica gel column chromatography (stationary phase: neutral silica gel, mobile phase: hexane/toluene), to thereby obtain Intermediate Product 1-1 (yielded amount: 30.2 g, yield: 90% by mass) represented by the following structural formula, as a pale yellow oily product.

[Chem.25]

Example 2

<Synthesis of Electrochromic Compound 2>
Electrochromic Compound 2 was synthesized according to the following scheme.

[Chem.27]

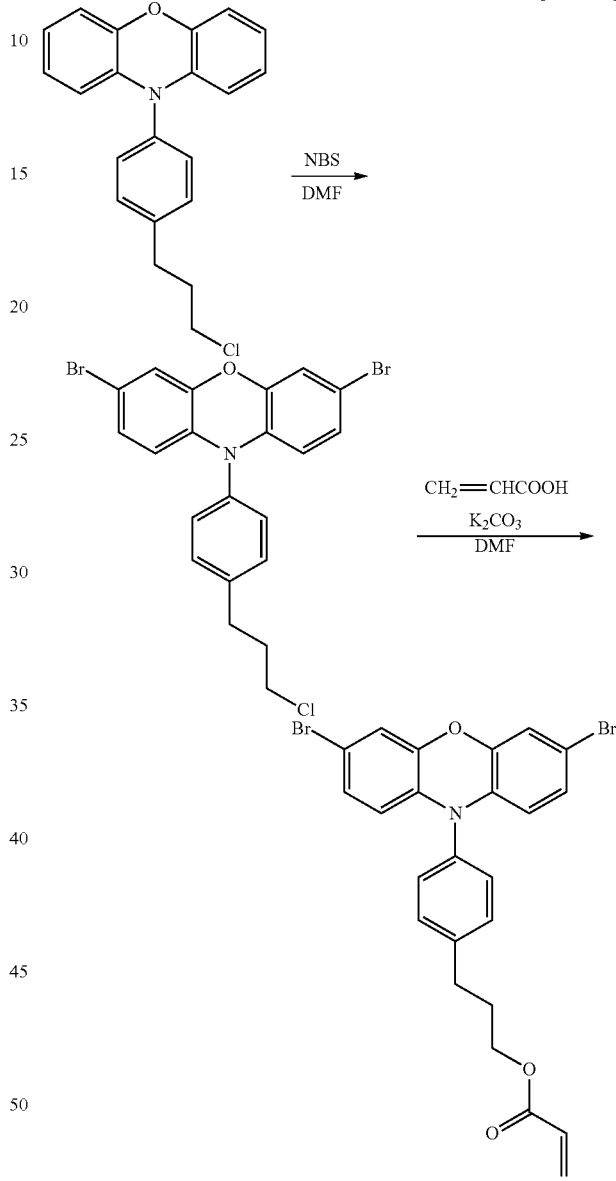

—Synthesis of Electrochromic Compound 1—

A flask purged with nitrogen was charged with Intermediate Product 1-1 (10.0 g, 29.8 mmol), acrylic acid (4.29 g, 59.6 mmol), potassium carbonate (6.21 g, 45.0 mmol), and N,N-dimethylformamide (DMF, 32 mL). The resultant mixture was heated and stirred for 20 hours at 80° C. The resultant solution was cooled to room temperature. To the resultant, ethyl acetate and water were added to separate an organic phase, and an aqueous phase was extracted 3 times with ethyl acetate. After washing the combined organic phase with water and then saturated brine, the organic phase was dried with sodium sulfate. The drying agent was separated through filtration, and the concentrated residue was purified by silica gel column chromatography (stationary phase: neutral silica gel, mobile phase: hexane/ethyl acetate) to thereby obtain Electrochromic Compound 1 (yielded amount: 10.6 g, yield: 96% by mass) as white solids.

MS spectrum (ESI) of Electrochromic Compound 1 was measured by means of a device (a device name: LCT Premier, measuring mode: ESI, ASAP probe) available from Waters Corporation. As a result, a theoretical value was 371.15 and a measured value was 371.2, confirming that Electrochromic Compound 1 was Electrochromic Compound 1 represented by the following structural formula (I).

[Chem.26]

Structural formula (I)

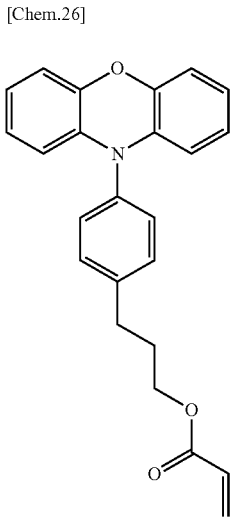

—Synthesis of Intermediate Product 2-1—

Intermediate Product 1-1 (5.04 g, 15 mmol) was dissolved in N,N-dimethylformamide (DMF, 100 mL), while cooling with ice. To the solution, N-bromosuccinimide (NBS, 5.61 g, 32 mmol) was gradually added. Thereafter, the resultant mixture was returned to room temperature, followed by stirring for 10 hours. To the reaction solution, water was added followed by toluene, to thereby separate an organic phase. An aqueous phase was extracted 3 times with toluene. The combined organic phase was washed with water, followed by saturated brine. The resultant was dried with sodium sulfate. The drying agent was separated through filtration. The residue obtained by condensing the filtrate was purified by silica gel column chromatography (stationary phase: neutral silica gel, mobile phase: toluene/hexane), to thereby obtain Intermediate Product 2-1 (yielded amount: 5.9 g, yield: 80% by mass), as pale yellow solids.

—Synthesis of Electrochromic Compound 2—

Electrochromic Compound 2 (yield: 93% by mass) was obtained in the same manner as in the synthesis of Electrochromic Compound 1 in Example 1, except that Intermediate Product 1-1 was replaced with Intermediate Product 2-1.

MS spectrum of Electrochromic Compound 2 was measured in the same manner as in Example 1. As a result, a theoretical value was 526.97 and a measured value was 527.0, confirming that Electrochromic Compound 2 was Electrochromic Compound 2 represented by the following structural formula (II).

[Chem.28]

Structural formula (II)

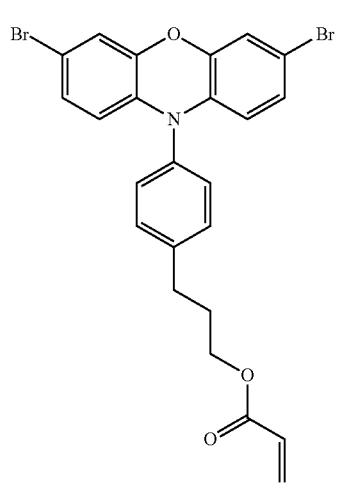

Example 3

<Synthesis of Electrochromic Compound 3>

Electrochromic Compound 3 was synthesized according to the following scheme.

[Chem.29]

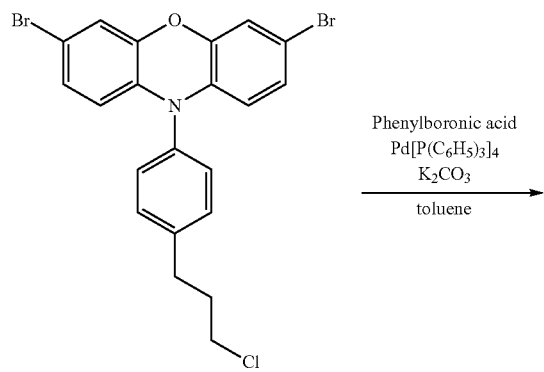

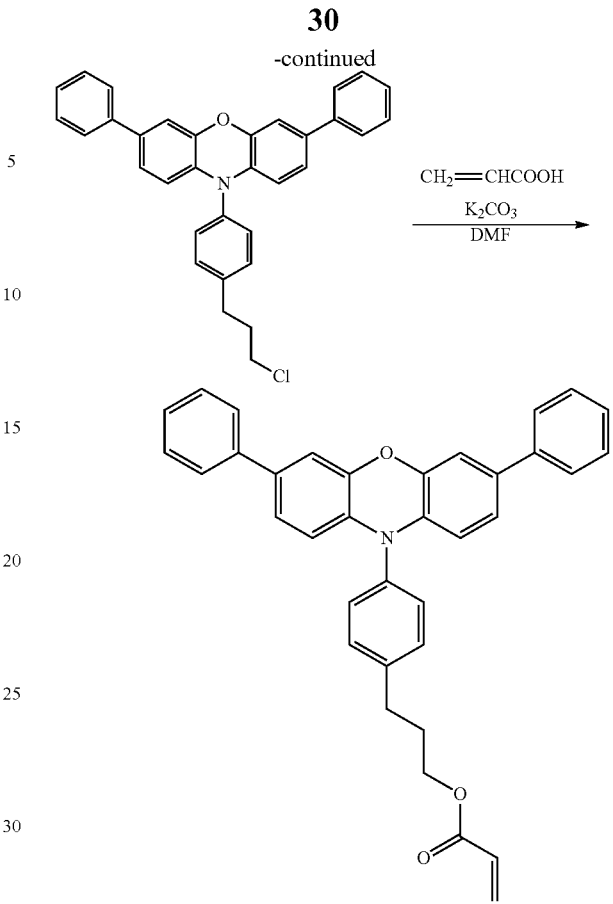

—Synthesis of Intermediate Product 3-1—

A flask purged with nitrogen was charged with Intermediate Product 2-1 (4.93 g, 10 mmol), phenylboronic acid (3.65 g, 30 mmol), potassium carbonate (8.28 g, 60 mmol), toluene (100 mL), water (30 mL), and ethanol (10 mL). After bubbling the resultant mixture with argon gas, tetrakis(triphenylphosphine)palladium(0) (116 mg, 0.1 mmol) was added. The resultant mixture was heated and stirred for 8 hours at 80° C.

To the reaction solution, water and toluene were sequentially added, to thereby separate an organic phase. An aqueous phase was extracted 3 times with toluene. The combined organic phase was washed with water, followed by saturated brine. The resultant was dried with sodium sulfate. The drying agent was separated through filtration, and the residue obtained by condensing the filtrate was purified by silica gel column chromatography (stationary phase: neutral silica gel, mobile phase: toluene), to thereby obtain Intermediate Product 3-1 (yielded amount: 4.1 g, yield: 83% by mass), as pale yellow solids.

—Synthesis of Electrochromic Compound 3—

Electrochromic Compound 3 was obtained in the same manner as in the synthesis of Electrochromic Compound 1 in Example 1, except that Intermediate Product 1-1 was replaced with Intermediate Product 3-1.

MS spectrum of Electrochromic Compound 3 was measured in the same manner as in Example 1. As a result, a theoretical value was 523.21 and a measured value was 523.2, confirming that Electrochromic Compound 3 was Electrochromic Compound 3 represented by the following structural formula (III).

[Chem.30]

Structural formula (III)

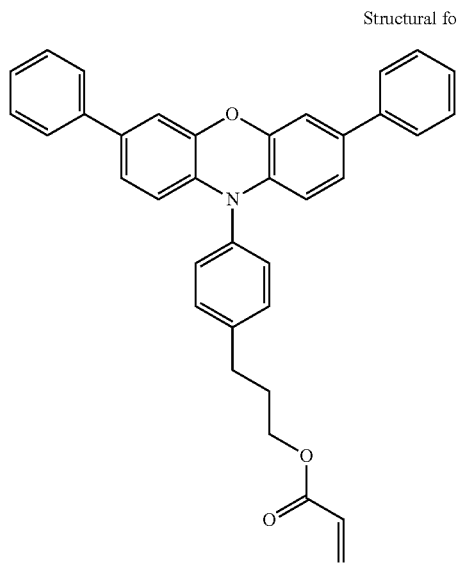

Example 4

<Synthesis of Electrochromic Compound 4>

Electrochromic Compound 4 was synthesized according to the following scheme.

[Chem.31]

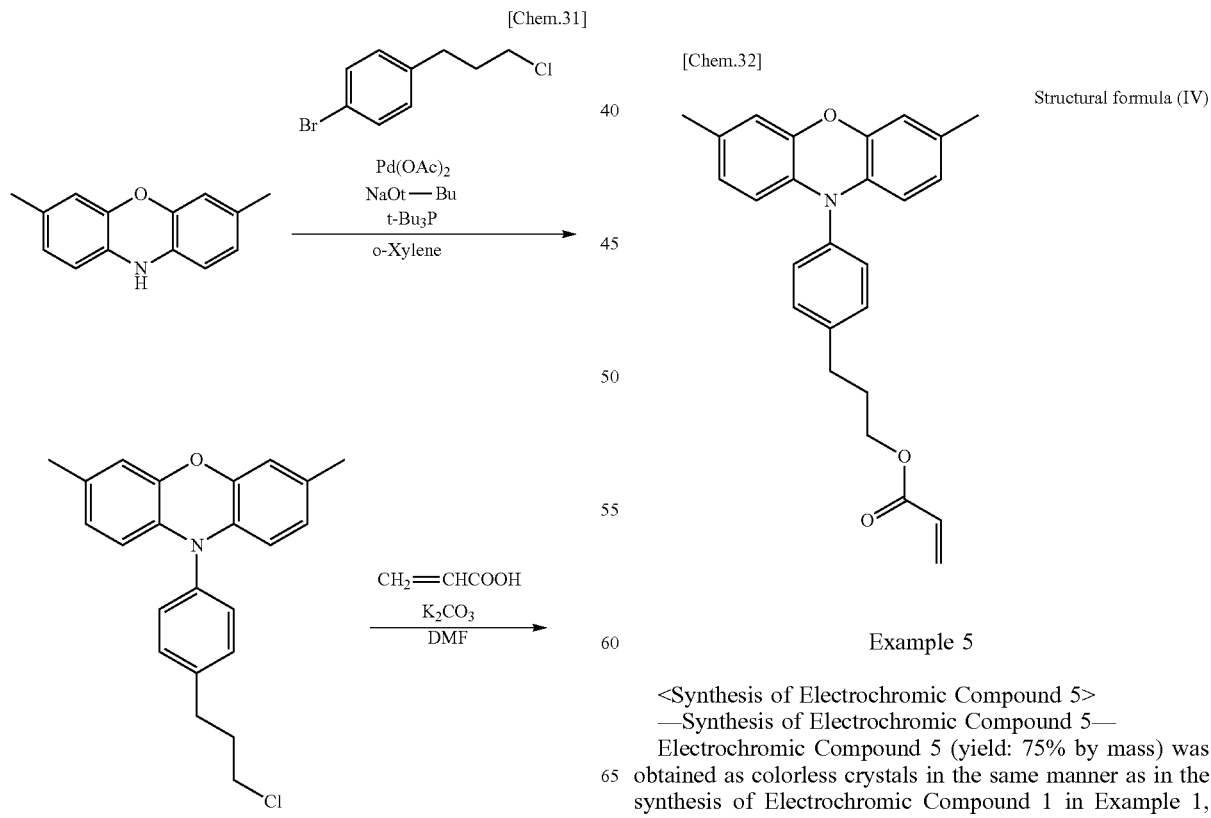

—Synthesis of Intermediate Product 4-1—

Intermediate Product 4-1 (yield: 80% by mass) was obtained in the same manner as in the synthesis of Intermediate Product 1-1 in Example 1, except that phenoxazine was replaced with 2,8-dimethylphenoxazine.

—Synthesis of Electrochromic Compound 4—

Electrochromic Compound 4 (yield: 98% by mass) was obtained in the same manner as in the synthesis of Electrochromic Compound 1 in Example 1, except that Intermediate Product 1-1 was replaced with Intermediate Product 4-1.

MS spectrum (ESI) of Electrochromic Compound 4 was measured in the same manner as in Example 1. As a result, a theoretical value was 399.18 and a measured value was 399.2, confirming that Electrochromic Compound 4 was Electrochromic Compound 4 represented by the following structural formula (IV).

[Chem.32]

Structural formula (IV)

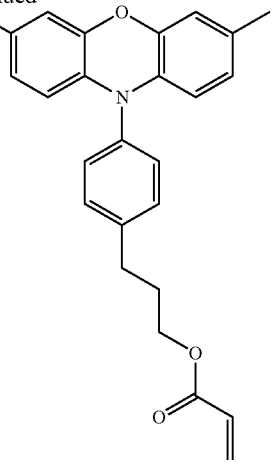

Example 5

<Synthesis of Electrochromic Compound 5>

—Synthesis of Electrochromic Compound 5—

Electrochromic Compound 5 (yield: 75% by mass) was obtained as colorless crystals in the same manner as in the synthesis of Electrochromic Compound 1 in Example 1, except that acrylic acid was replaced with methacrylic acid.

MS spectrum (ESI) of Electrochromic Compound 5 was measured in the same manner as in Example 1. As a result, a theoretical value was 385.17 and a measured value was 385.2, confirming that Electrochromic Compound 5 was Electrochromic Compound 5 represented by the following structural formula (V).

[Chem.33]

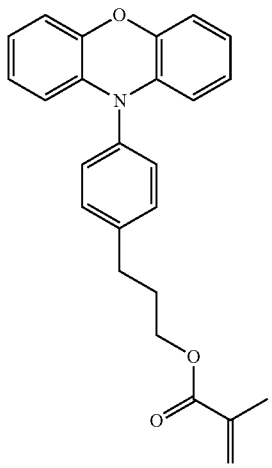

Structural formula (V)

Example 6

<Synthesis of Electrochromic Compound 6>
—Synthesis of Electrochromic Compound 6—

Electrochromic Compound 6 (yield: 90% by mass) was obtained as colorless crystals in the same manner as in the synthesis of Electrochromic Compound 1 in Example 1, except that Intermediate Product 1-1 was replaced with Intermediate Product 4-1, and acrylic acid was replaced with methacrylic acid.

MS spectrum (ESI) of Electrochromic Compound 6 was measured in the same manner as in Example 1. As a result, a theoretical value was 413.20 and a measured value was 413.3, confirming that Electrochromic Compound 6 was Electrochromic Compound 6 represented by the following structural formula (VI).

[Chem.34]

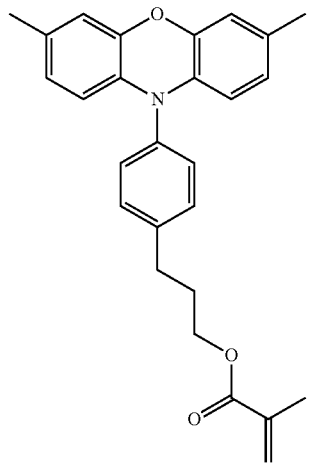

Structural formula (VI)

Example 7

<Preparation Example 7 of Electrochromic Compound 7>
Electrochromic Compound 7 was synthesized according to the following scheme.

[Chem.35]

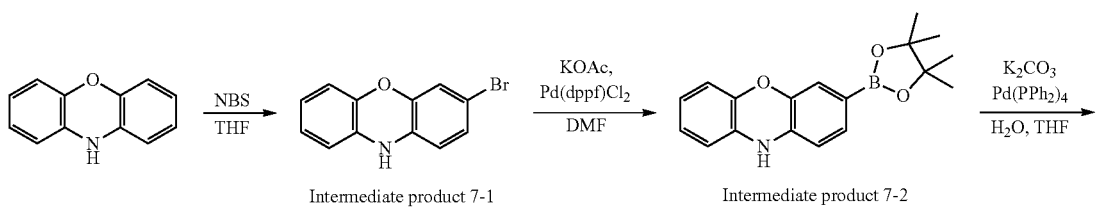

[Chem.36]

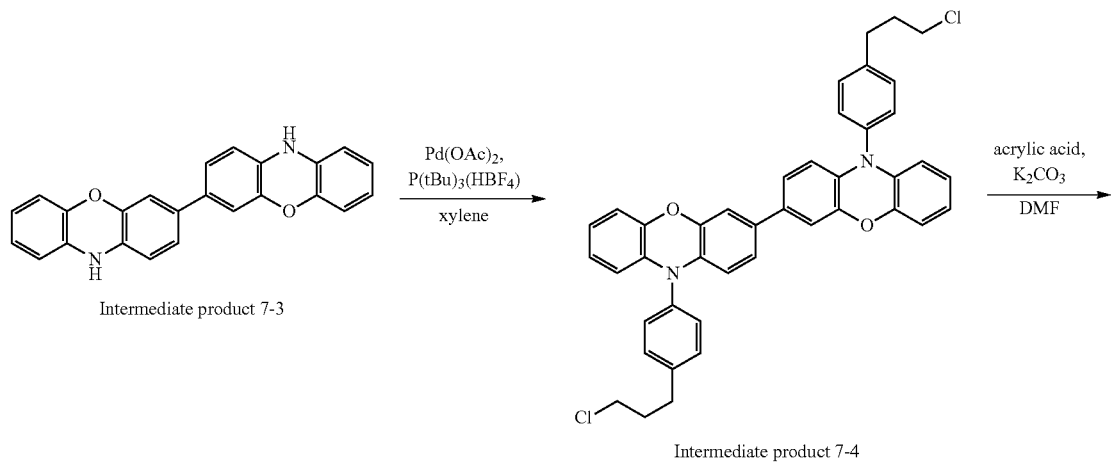

Intermediate product 7-3

Intermediate product 7-4

[Chem.37]

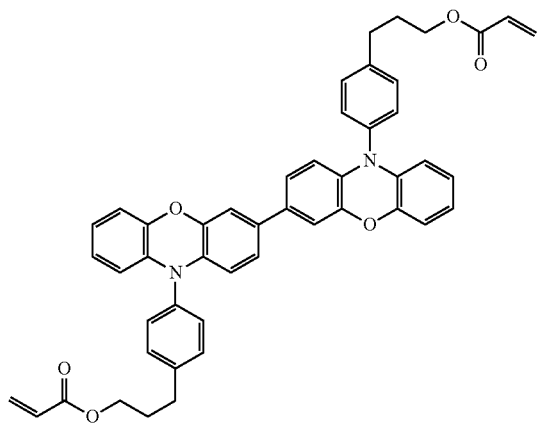

Electrochromic Compound 7

—Synthesis of Intermediate Product 7-1—

While cooling with ice, phenoxazine (31.1 g, 170 mmol) was added to tetrahydrofuran (600 mL), and a N-bromosuccinimide (30.2 g, 170 mmol) tetrahydrofuran (450 mL) solution was gradually added dropwise to the resultant mixture. After the dropwise addition, the resultant was returned to room temperature, and was stirred for 1.5 hours. After adding ethyl acetate to the reaction solution, an organic layer was washed with water. After drying the resultant with anhydrous sodium sulfate, the drying agent was separated through filtration. The residue obtained by removing the solvent under reduced pressure was purified by silica gel column chromatography (stationary phase: neutral silica gel, mobile phase: ethyl acetate/hexane), to thereby obtain Intermediate Product 7-1 (yielded amount: 25.6 g, yield: 19% by mass).

—Synthesis of Intermediate Product 7-2—

A 1 L flask was charged with Intermediate Product 7-1 (15.9 g, 60.7 mmol), bispina-colatodiboron (23.9 g, 94.1 mmol), potassium acetate (18.6 g, 189 mmol), and Pd(dppf)Cl$_2$ (2.43 g, 3.28 mmol). After purging the system with nitrogen, dry DMF (600 mL) was added to the flask, followed by stirring for 2 hours at 85° C. After removing the solvent under reduced pressure, ethyl acetate was added to the mixture, and insoluble matter was separated through filtration. After washing the solution with water, the resultant was dried with anhydrous sodium sulfate. The drying agent was separated through filtration, and the residue obtained by removing the solvent under reduced pressure was purified by silica gel column chromatography (stationary phase: neutral silica gel, mobile phase: ethyl acetate/hexane), to thereby obtain Intermediate Product 7-2 (yielded amount: 8.7 g, yield: 47% by mass).

—Synthesis of Intermediate Product 7-3—

With reference to the synthesis of Intermediate Product 3-1, Intermediate Product 7-3 was obtained from Intermediate Product 7-1 and Intermediate Product 7-2.

—Synthesis of Intermediate Product 7-4—

With reference to the synthesis of Intermediate Product 1-1, Intermediate Product 7-4 was obtained from Intermediate Product 7-3.

—Synthesis of Electrochromic Compound 7—

Electrochromic Compound 7 was obtained as pale yellow solids in the same manner as in the synthesis of Electrochromic Compound 1.

Example 8

<Production of Electrochromic Display Element 1>
—Formation of Electrochromic Layer on First Electrode—

In order to form an electrochromic layer on a first electrode, an electrochromic composition having the following formulation was prepared.

(Formulation)
Electrochromic Compound 1: 50 parts by mass
IRGACURE184 (available from BASF Japan): 5 parts by mass
PEG400 diacrylate having bifunctional acrylate (PEG400DA, available from Nippon Kayaku Co., Ltd.): 50 parts by mass
Methyl ethyl ketone: 900 parts by mass The obtained electrochromic composition was coated onto an ITO glass substrate (40 mm×40 mm, thickness: 0.7 mm, ITO film thickness: about 100 nm) serving as a first electrode by spin coating. The obtained coated film was irradiated at 10 mW for 60 seconds by means of a UV irradiation device (SPOT CURE, available from USHIO INC.). Thereafter, the coated film was annealed for 10 minutes at 60° C., to thereby form a cross-linked electrochromic layer having an average thickness of 400 rm.

—Formation of Antideterioration Layer on Second Electrode—

A titanium oxide nanoparticle dispersion liquid (product name: SP210, available from SHOWA DENLO K.K., average particle diameter: about 20 nm) was applied as an antideterioration layer onto an ITO glass substrate (40 mm×40 mm, thickness: 0.7 mm, ITO film thickness: about 100 nm) serving as a second electrode by spin coating. The coated film was annealed for 15 minutes at 120° C., to thereby form a nanostructure semiconductive material formed of a titanium oxide particle film having a thickness of 1.0 m.

—Filling with Electrolyte—

An electrolytic solution having the following formulation was prepared.

IRGACURE184 (available from BASF Japan): 5 parts by mass
PEG400DA (available from Nippon Kayaku Co., Ltd.): 100 parts by mass
1-Ethyl-3-methylimidazolium tetracyanoborate (available from Merck KGaA): 50 parts by mass 30 mg of the obtained electrolytic solution was weighted with a micropipette, and was dripped onto the ITO glass substrate having the antideterioration layer. Onto the thus-obtained ITO glass substrate, the ITO glass substrate having the cross-linked electrochromic layer was bonded so as to leave drawing parts for the electrodes, to thereby produce a bonded element.

The obtained bonded element was irradiated at 10 mW for 60 seconds by means of a UV (wavelength: 250 nm) irradiation device (SPOT CURE, available from USHIO INC.), to thereby produce an electrochromic display element.

<Coloring and Decoloring>

Coloring and decoloring of the produced electrochromic display element were confirmed. Specifically, voltage of minus 2 V was applied between the drawing part of the first electrode layer and the drawing part of the second electrode layer for 5 seconds. As a result, coloring in magenta originated from Electrochromic Compound 1 of the electrochromic layer was confirmed in the area where the first electrode layer and the second electrode layer were overlapped.

Voltage of plus 2 V was applied between the drawing part of the first electrode and the drawing part of the second electrode for 5 seconds. As a result, it was confirmed that the color of the area where the first electrode layer and the second electrode layer were overlapped was decolored and turned into transparent. Transmission spectrums at the time of coloring and decoloring were measured by means of USB4000 available from Ocean Optics, Inc. The transmission spectrums of the electrochromic display element of Example 8 for coloring and decoloring are depicted in FIG. 4 (dashed line: decoloring, solid line: coloring).

<Durability to Repetitive Use>

A coloring and decoloring operation including applying voltage of minus 2 V for 5 seconds and applying voltage of plus 2 V for 5 seconds was performed and repeated on the produced electrochromic display element 500 times. In this procedure, the maximum absorption in a visible region (from 400 nm through 800 nm) was determined as Xmax (in this case, 540 nm). A change in absorbance between initial absorbance and absorbance after 500-times repetitions was measured by means of USB4000 available from Ocean Optics, Inc., and evaluated based on the following evaluation criteria. The results are presented in Table 1.

(Evaluation Criteria)

A: The absorbance of Xmax was 90% or greater compared to the initial state.

B: The absorbance of Xmax was 80% or greater but less than 90% compared to the initial state.

C: The absorbance of Xmax was 50% or greater but less than 80% compared to the initial state.

D: The absorbance of Xmax was less than 50% compared to the initial state.

Examples 9 to 14

Electrochromic display elements of Examples 9 to 14 were produced in the same manner as in Example 8, except that Electrochromic Compound 1 was replaced with Electrochromic Compounds 2 to 7 depicted in Table 1. The produced electrochromic display elements were evaluated in terms of a color and durability to repetitive use in the same manner as in Example 8. The results are presented in Table 1.

Comparative Example 1

An electrochromic display element of Comparative Example 1 was produced in the same manner as in Example 8, except that Electrochromic Compound 1 was replaced with a compound represented by the following structural formula (VII). The produced electrochromic display element was evaluated in terms of a color and durability to repetitive use in the same manner as in Example 8. The results are presented in Table 1.

[Chem.38]

Structural formula (VII)

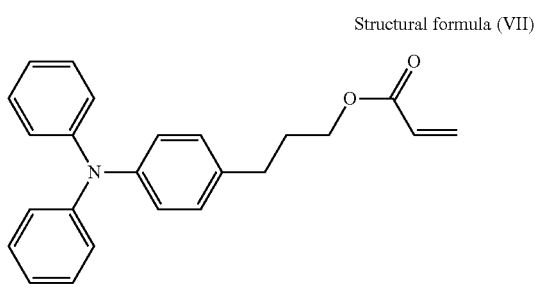

Comparative Example 2

An electrochromic display element of Comparative Example 2 was produced in the same manner as in Example 8, except that Electrochromic Compound 1 was replaced with a compound represented by the following structural formula (VIII). The produced electrochromic display element was evaluated in terms of a color and durability to repetitive use in the same manner as in Example 8. The results are presented in Table 1.

[Chem.39]

Structural formula (VIII)

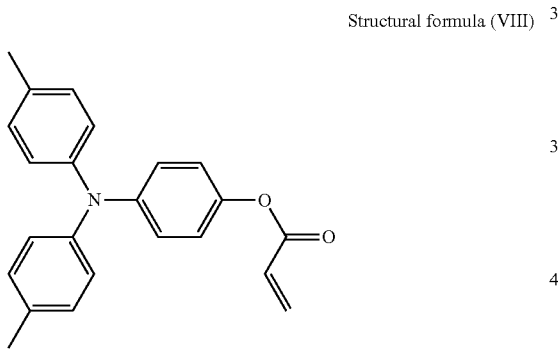

TABLE 1

|  |  | Compound | Color | Durability to repetitive use |
|---|---|---|---|---|
| Ex. | 8 | Electrochromic Compound 1 | Magenta | A |
|  | 9 | Electrochromic Compound 2 | Cyan | A |
|  | 10 | Electrochromic Compound 3 | Green | B |
|  | 11 | Electrochromic Compound 4 | Purple | A |
|  | 12 | Electrochromic Compound 5 | Magenta | A |
|  | 13 | Electrochromic Compound 6 | Purple | A |
|  | 14 | Electrochromic Compound 8 | Magenta | A |
| Comp. Ex. | 1 | Structural formula VII | Blue | D |
|  | 2 | Structural formula VIII | Blue | C |

It was found from the results presented in Table 1 that Examples 8 to 14 gave the electrochromic display elements that had excellent colors and durabilities to repetitive use, compared to Comparative Examples 1 and 2.

FIG. 5 depicts chromaticity coordinates of Electrochromic Compounds 1 to 4 used in Examples 8 to 11. As illustrated in FIG. 5, all of the dyes were colorless and present near a starting point when decolored, but chromaticities went up linearly when colored. Moreover, it was observed that various colors were obtained depending on the positions of the substituents, and Electrochromic Compounds 1 to 4 had excellent colors.

REFERENCE SIGNS LIST 1 first electrode
2 second electrode
3 electrolyte
4 electrochromic compound
10 first electrode
12 second electrode
13 electrolyte
14a electrochromic composition
15 display layer
18 electrochromic display element
20 first electrode
22 second electrode
23 electrolyte
24a electrochromic composition
25 display layer
26 white reflection layer
28 electrochromic display element

The invention claimed is:

1. An electrochromic display element, comprising:
a first electrode;
a second electrode; and
an electrolyte placed between the first electrode and the second electrode,
wherein the first electrode comprises
a polymerizable compound, and
an electrochromic compound of formula (I) or (II):

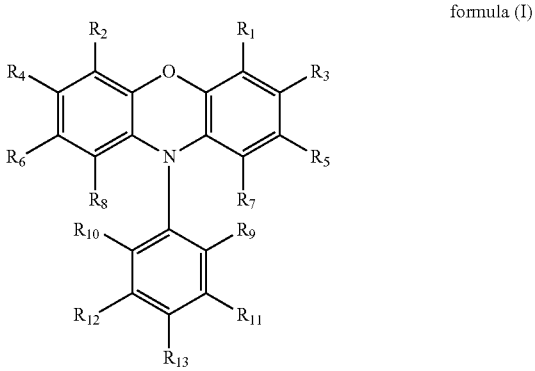

formula (I)

-continued formula (II)

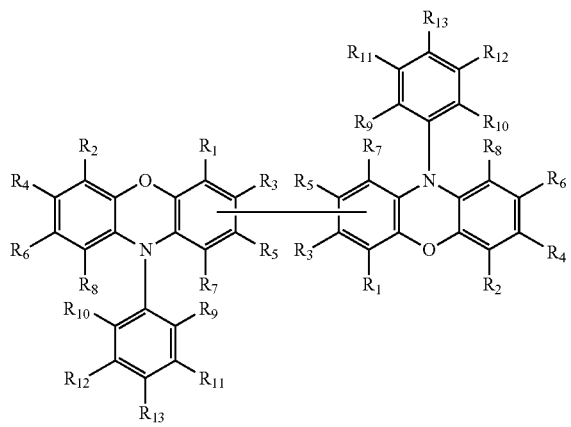

wherein R₁ to R₁₃ are each independently a hydrogen atom, a halogen atom, a monovalent organic group, or a polymerizable functional group, and at least one of R₁ to R₁₃ is a polymerizable functional group; and wherein the polymerizable compound is different from the electrochromic compound.

2. The electrochromic display element according to claim 1, wherein, when any of R₁ to R₁₃ is the monovalent organic group, the monovalent organic group is an alkyl group, an alkenyl group, an alkynyl group, an aryl group, a heteroaryl group, an alkoxy group, an aryloxy group, or a heteroaryloxy group.

3. The electrochromic display element according to claim 2, wherein the polymerizable compound is a bifunctional or higher polymerizable compound.

4. The electrochromic display element according to claim 1, wherein R₃ and R₄ are each a halogen atom, a monovalent organic group, or a polymerizable functional group.

5. The electrochromic display element according to claim 4, wherein the polymerizable compound is a bifunctional or higher polymerizable compound.

6. The electrochromic display element according to claim 1, wherein, when any of R₁ to R₁₃ is the polymerizable functional group, the polymerizable functional group is an alkyl group, an aryl group, or an aryl group substituted with an alkyl group.

7. The electrochromic display element according to claim 6, wherein the polymerizable compound is a bifunctional or higher polymerizable compound.

8. The electrochromic display element according to claim 1, wherein, when any of R₁ to R₁₃ is the polymerizable functional group, the polymerizable functional group is an acryloyl group or a methacryloyl group.

9. The electrochromic display element according to claim 8, wherein the polymerizable compound is a bifunctional or higher polymerizable compound.

10. The electrochromic display element according to claim 1, wherein the polymerizable compound is a bifunctional or higher polymerizable compound.

11. The electrochromic display element according to claim 1, wherein the electrochromic compound has the formula (I).

12. The electrochromic display element according to claim 1, wherein the electrochromic compound has the formula (II).

* * * * *